US011712507B2

(12) United States Patent
Peterson et al.

(10) Patent No.: US 11,712,507 B2
(45) Date of Patent: Aug. 1, 2023

(54) MANIFOLD FOR A MEDICAL/SURGICAL WASTE COLLECTION SYSTEM WITH A MATERIAL COLLECTION VOLUME FOR COLLECTING MATERIAL ENTRAINED WITHIN FLUID

(71) Applicant: Stryker Corporation, Kalamazoo, MI (US)

(72) Inventors: Michael Peterson, Richland, MI (US); Anshul Shandillya, Uttar Pradesh (IN); Stephen Isham, Mattawan, MI (US); Stephen J. Reasoner, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 871 days.

(21) Appl. No.: 16/493,100

(22) PCT Filed: Mar. 15, 2018

(86) PCT No.: PCT/US2018/022592
§ 371 (c)(1),
(2) Date: Sep. 11, 2019

(87) PCT Pub. No.: WO2018/170233
PCT Pub. Date: Sep. 20, 2018

(65) Prior Publication Data
US 2020/0061255 A1 Feb. 27, 2020

Related U.S. Application Data

(60) Provisional application No. 62/472,969, filed on Mar. 17, 2017.

(51) Int. Cl.
*A61M 1/00* (2006.01)
*A61M 37/00* (2006.01)
(Continued)

(52) U.S. Cl.
CPC ............ *A61M 1/79* (2021.05); *A61M 2202/09* (2013.01); *A61M 2205/125* (2013.01); *A61M 2205/7545* (2013.01); *A61M 2205/7563* (2013.01)

(58) Field of Classification Search
CPC ........ A61M 1/00; A61M 37/00; A61M 31/00; A61M 1/0001; A61M 1/0023;
(Continued)

(56) References Cited

U.S. PATENT DOCUMENTS 2,709,681 A 5/1955 Wright
4,643,197 A 2/1987 Greene et al.
(Continued)

FOREIGN PATENT DOCUMENTS

CN 102333555 A 1/2012
DE 202006008306 U1 7/2006
(Continued)

OTHER PUBLICATIONS

English language abstract for CN 102333555 A extracted from espacenet.com database on Dec. 2, 2021, 2 pages.
(Continued)

*Primary Examiner* — Benjamin J Klein
*Assistant Examiner* — Ilya Y Treyger
(74) *Attorney, Agent, or Firm* — Howard & Howard Attorneys PLLC

(57) ABSTRACT

A manifold for a medical/surgical waste collection system. An outlet opening and a fitting are in fluid communication with a manifold volume within a housing. The fitting receives a suction line. A filter element with porous features is disposed within the housing such that a fluid communication path is established across the filter element. The porous features trap material entrained within the fluid. A material collection volume is at least partially distal to and
(Continued)

below a bottom of the filter element. As the fluid and the material is drawn through the fluid communication path, the material collects within the material collection volume. A flow diverter may be positioned within the housing for directing the material towards the material collection volume. The material collection volume may be at least partially defined by a tissue trap removably coupled to the housing.

18 Claims, 14 Drawing Sheets

(51) Int. Cl.
 *A61M 31/00* (2006.01)
 *A61B 17/20* (2006.01)
(58) Field of Classification Search
 CPC .............. A61M 1/0058; A61M 5/1415; A61M 2205/3331; A61B 17/20
 See application file for complete search history.

(56) References Cited

U.S. PATENT DOCUMENTS

| | | | |
|---|---|---|---|
| 5,108,381 A | 4/1992 | Kolozsi | |
| 5,624,418 A | 4/1997 | Shepard | |
| 6,027,490 A | 2/2000 | Radford et al. | |
| 6,149,812 A | 11/2000 | Erickson | |
| 6,331,246 B1 | 12/2001 | Beckham et al. | |
| 6,488,675 B1 | 12/2002 | Radford et al. | |
| 6,592,769 B1 | 7/2003 | Erickson | |
| 6,752,795 B2 | 6/2004 | Cull | |
| 6,902,673 B2 | 6/2005 | Smit et al. | |
| 7,163,618 B2 | 1/2007 | Beckham et al. | |
| 7,182,599 B2 | 2/2007 | Stone et al. | |
| 7,497,340 B2 | 3/2009 | Hershberger et al. | |
| 7,572,236 B2 | 8/2009 | Quick et al. | |
| 7,615,037 B2 | 11/2009 | Murray et al. | |
| 7,621,898 B2 | 11/2009 | Lalomia et al. | |
| 7,981,051 B2 | 7/2011 | Quick et al. | |
| 8,088,079 B2 | 1/2012 | Kaye et al. | |
| 8,088,291 B2 | 1/2012 | Hershberger et al. | |
| 8,216,199 B2 | 7/2012 | Murray et al. | |
| 8,317,725 B2 | 11/2012 | Quick et al. | |
| 8,424,685 B2 | 4/2013 | Smit et al. | |
| 8,518,002 B2 | 8/2013 | Murray et al. | |
| 8,668,464 B2 | 3/2014 | Kensy et al. | |
| 8,740,866 B2 | 6/2014 | Reasoner et al. | |
| 8,801,682 B2 | 8/2014 | Kensy | |
| 8,915,864 B2 | 12/2014 | Quick et al. | |
| 8,915,897 B2 | 12/2014 | Murray et al. | |
| 9,056,158 B2 | 6/2015 | Gavlak et al. | |
| 9,089,801 B1 | 7/2015 | Gavlak et al. | |
| 9,206,387 B2 | 12/2015 | Llull et al. | |
| 9,260,697 B2 | 2/2016 | Cimino et al. | |
| 9,296,984 B2 | 3/2016 | Cimino et al. | |
| 9,579,428 B1 | 2/2017 | Reasoner et al. | |
| 9,770,541 B2 | 9/2017 | Carr et al. | |
| 9,782,524 B2 | 10/2017 | Reasoner et al. | |
| 9,795,723 B2 | 10/2017 | Gavlak et al. | |
| 10,369,269 B2 | 8/2019 | Santora et al. | |
| 10,406,265 B2 | 9/2019 | Kensy et al. | |
| 2001/0040123 A1 | 11/2001 | Beckham | |
| 2005/0139532 A1 | 6/2005 | Hershberger et al. | |
| 2005/0171495 A1 | 8/2005 | Austin et al. | |
| 2005/0187529 A1 | 8/2005 | Reasoner et al. | |
| 2005/0189283 A1 | 9/2005 | Smit et al. | |
| 2007/0032740 A1 | 2/2007 | Quick et al. | |
| 2007/0135778 A1 | 6/2007 | Murray et al. | |
| 2007/0135779 A1 | 6/2007 | Lalomia et al. | |
| 2007/0270714 A1 | 11/2007 | Cushner et al. | |
| 2008/0053539 A1 | 3/2008 | Hershberger et al. | |
| 2008/0082021 A1 | 4/2008 | Ichikawa et al. | |
| 2008/0179344 A1* | 7/2008 | Michaels ................ G01F 23/02 222/335 |
| 2011/0104800 A1 | 5/2011 | Kensy et al. | |
| 2011/0106029 A1 | 5/2011 | Garren et al. | |
| 2011/0245715 A1 | 10/2011 | Quick et al. | |
| 2012/0189973 A1 | 7/2012 | Schwenk | |
| 2013/0199975 A1 | 8/2013 | Stone | |
| 2013/0206670 A1 | 8/2013 | Smit et al. | |
| 2014/0323914 A1 | 10/2014 | VanderWoude et al. | |
| 2014/0336599 A1 | 11/2014 | Patel et al. | |
| 2014/0338529 A1 | 11/2014 | Reasoner et al. | |
| 2015/0080760 A1 | 3/2015 | Quick et al. | |
| 2015/0209491 A1 | 7/2015 | Cushner et al. | |
| 2015/0224237 A1 | 8/2015 | Reasoner et al. | |
| 2015/0352256 A1 | 12/2015 | Cimino et al. | |
| 2015/0359941 A1 | 12/2015 | Llull et al. | |
| 2015/0368603 A1 | 12/2015 | Cimino et al. | |
| 2016/0008407 A1 | 1/2016 | Cimino et al. | |
| 2016/0030486 A1 | 2/2016 | Cimino et al. | |
| 2016/0160172 A1 | 6/2016 | Cimino et al. | |
| 2016/0208211 A1 | 7/2016 | Cimino et al. | |
| 2016/0331282 A1 | 11/2016 | Satish et al. | |
| 2017/0043064 A1 | 2/2017 | Reasoner et al. | |
| 2018/0000998 A1 | 1/2018 | Carr et al. | |

FOREIGN PATENT DOCUMENTS

| | | | |
|---|---|---|---|
| WO | | 9726928 A1 | 7/1997 |
| WO | | 2004000180 A2 | 12/2003 |
| WO | | 2005042061 A1 | 5/2005 |
| WO | | 2005079947 A2 | 9/2005 |
| WO | | 2006014224 A2 | 2/2006 |
| WO | | 2006019406 A1 | 2/2006 |
| WO | | 2007019445 A1 | 2/2007 |
| WO | | 2007070570 A2 | 6/2007 |
| WO | | 2007079319 A2 | 7/2007 |
| WO | | 2007103842 A2 | 9/2007 |
| WO | | 2007137219 A2 | 11/2007 |
| WO | | 2009149691 A2 | 12/2009 |
| WO | | 2009149691 A3 | 5/2010 |
| WO | | 2011009723 A1 | 1/2011 |
| WO | | 2011082389 A1 | 7/2011 |
| WO | WO 2013/090579 | * | 12/2011 |
| WO | | 2012006587 A2 | 1/2012 |
| WO | | 2012064542 A2 | 5/2012 |
| WO | | 2013090579 A1 | 6/2013 |
| WO | | 2013106655 A1 | 7/2013 |
| WO | | 2014039697 A1 | 3/2014 |
| WO | | 2014066337 A2 | 5/2014 |
| WO | | 2014110448 A1 | 7/2014 |
| WO | | 2015035221 A1 | 3/2015 |
| WO | | 2015175743 A1 | 11/2015 |
| WO | | 2016187071 A1 | 11/2016 |
| WO | | 2016209820 A1 | 12/2016 |
| WO | | 2017127541 A1 | 7/2017 |

OTHER PUBLICATIONS

International Search Report for Application No. PCT/US2018/022592 dated Jun. 11, 2018, 5 pages.
English language abstract and machine-assisted English translation for DE 20 2006 008 306 extracted from espacenet.com database on Sep. 19, 2019, 5 pages.
English language abstract for WO 2009/149691 extracted from espacenet.com database on Sep. 19, 2019, 1 page.
English language abstract for WO 2011/009723 extracted from espacenet.com database on Sep. 19, 2019, 1 page.

* cited by examiner

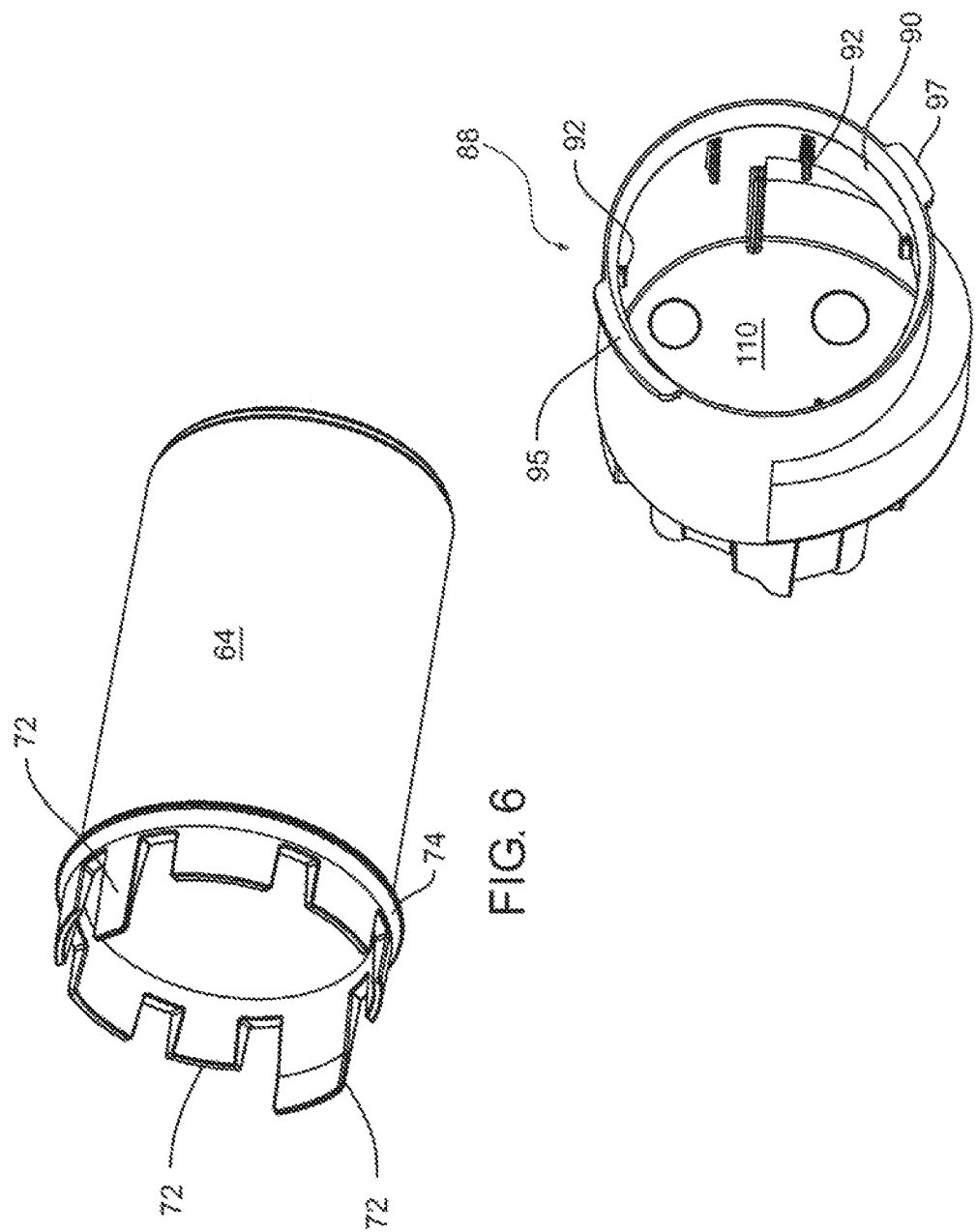

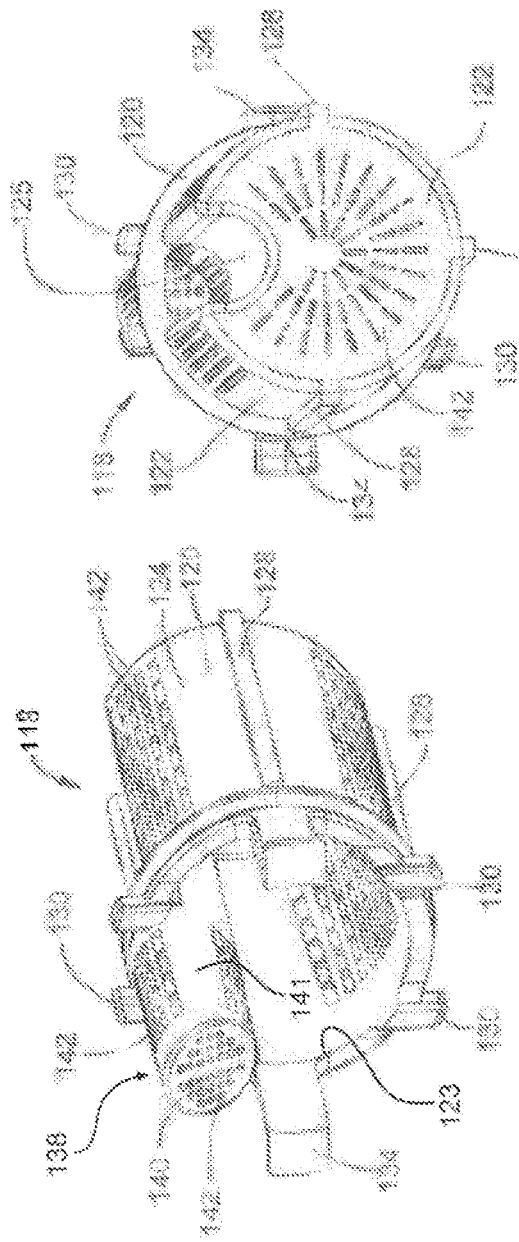
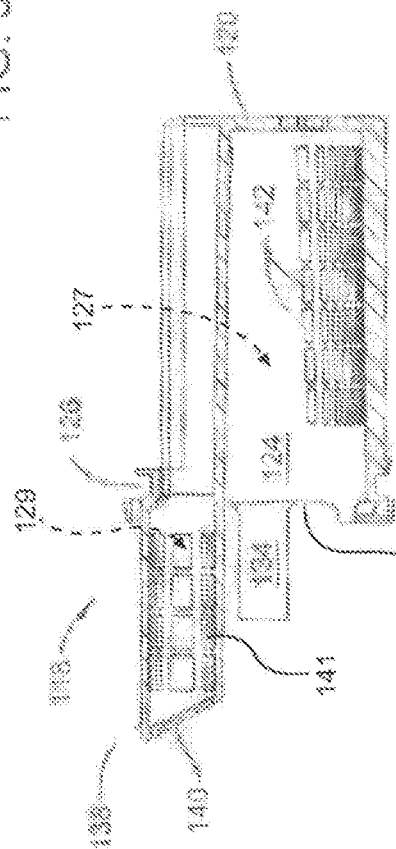

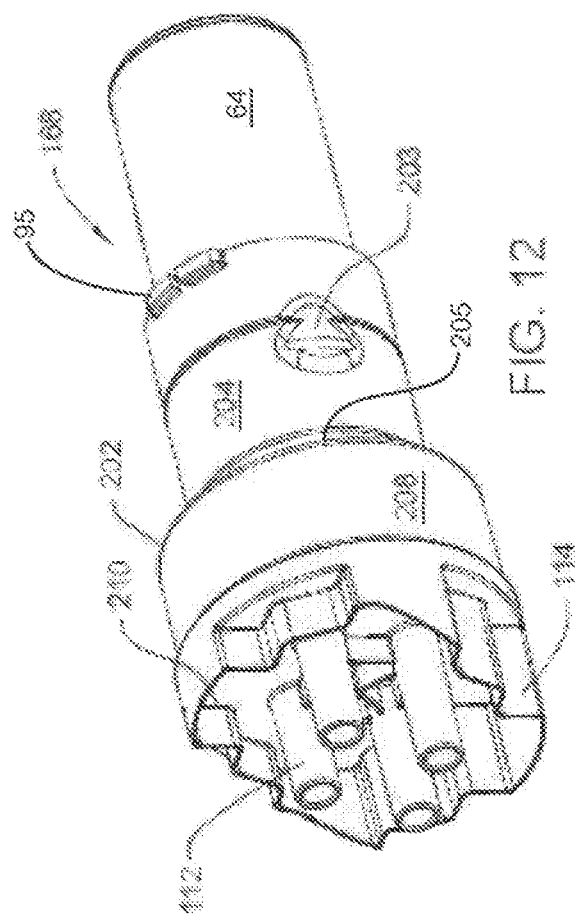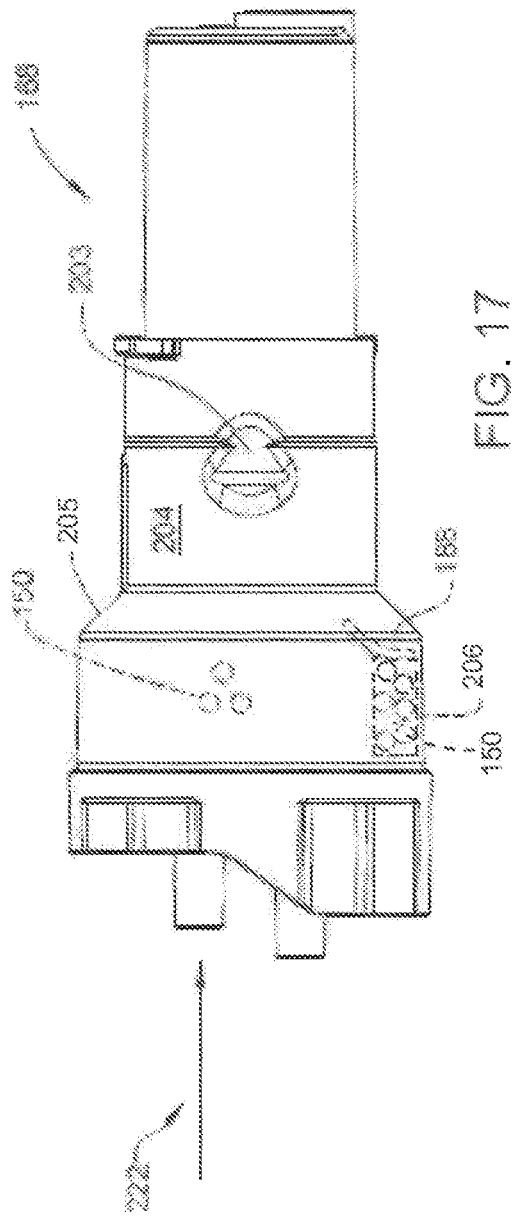

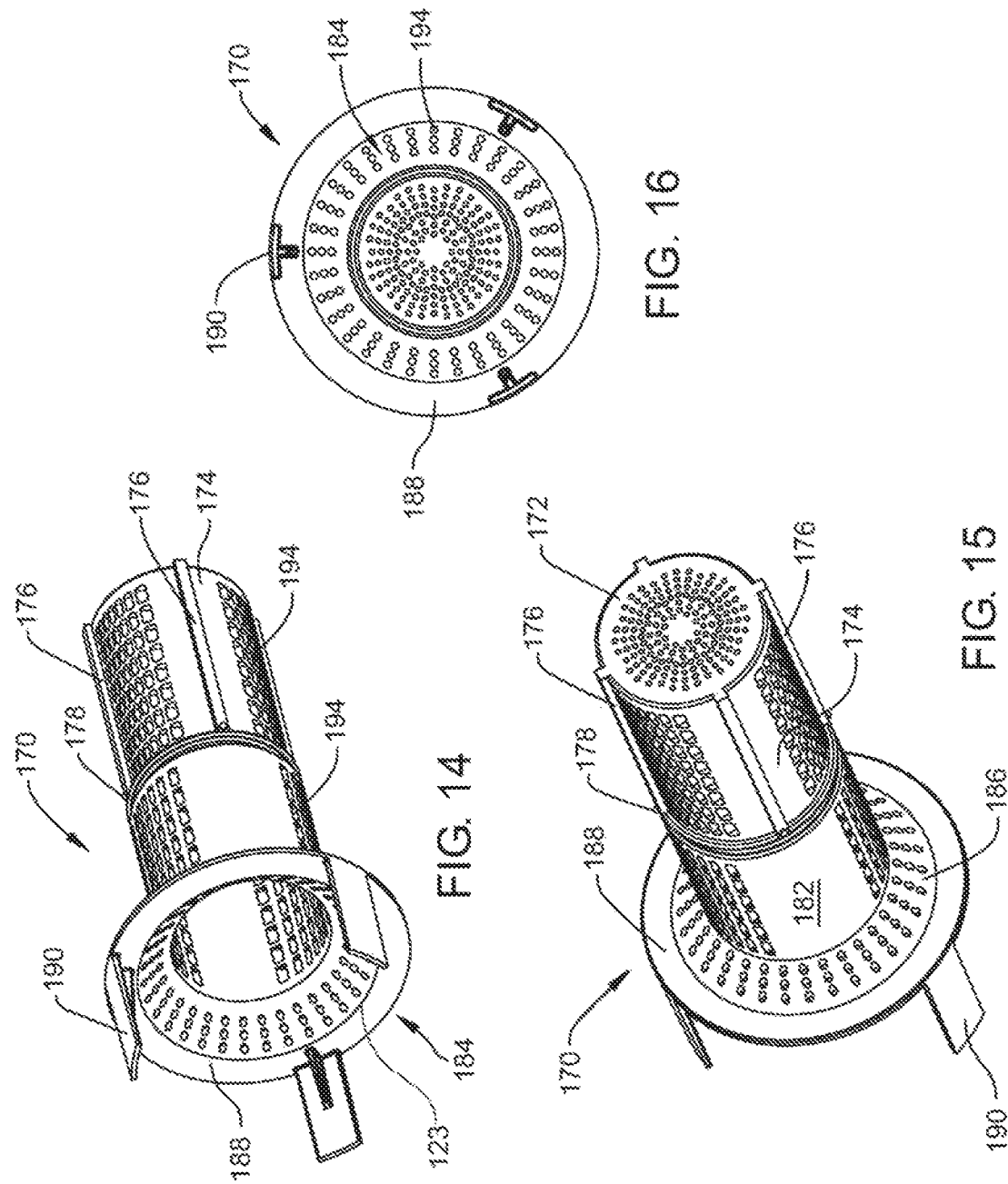

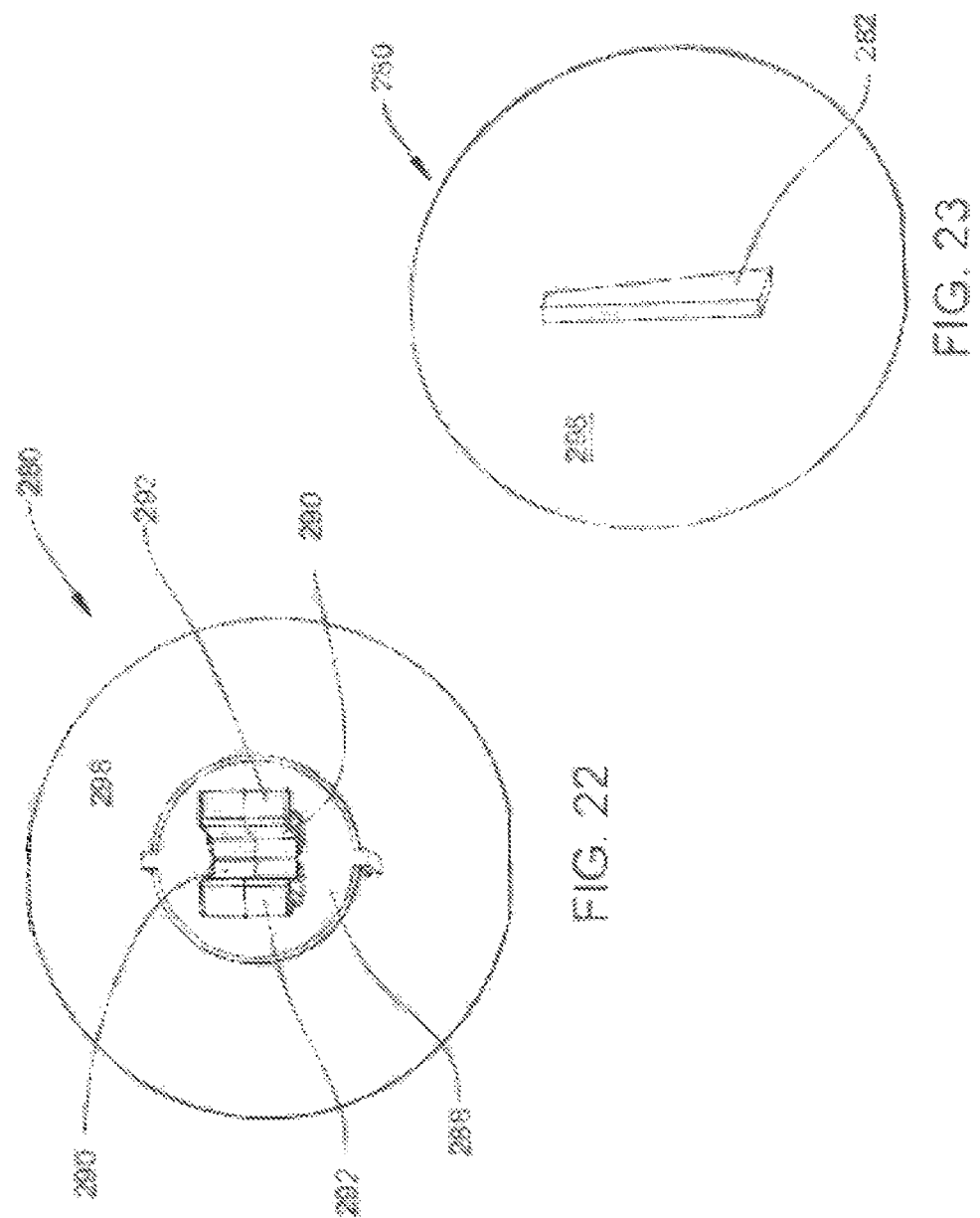

MANIFOLD FOR A MEDICAL/SURGICAL WASTE COLLECTION SYSTEM WITH A MATERIAL COLLECTION VOLUME FOR COLLECTING MATERIAL ENTRAINED WITHIN FLUID

CROSS-REFERENCE TO RELATED APPLICATIONS

U.S. National Phase of PCT/US2018/022592, filed Mar. 15, 2018, which claims the benefit of U.S. Provisional Application 62/472,969 filed on Mar. 17, 2017, the entire contents of each are hereby incorporated by reference.

FIELD OF THE DISCLOSURE

The disclosure relates generally to systems and methods for collecting waste generated during a surgical procedure. More particularly, but not exclusively, the disclosure relates to a manifold for a medical/surgical waste collection system that reduces the likelihood that waste entrained within the flow of fluid disrupts operation of the medical/surgical waste collection system.

BACKGROUND OF THE DISCLOSURE

A byproduct of some medical and surgical procedures is the generation of liquid, semisolid, and solid waste material. The liquid waste material may include bodily fluids, such as blood, and irrigating solution(s) introduced to the surgical site at which the procedure is performed. Solid and semi-solid waste generated during a procedure may include bits of tissue and pieces of the surgical material present at the site. The waste, regardless of its phase, is ideally collected upon generation so it neither fouls the surgical site nor becomes a biohazard in the operating room or other location at which the procedure is being performed.

Known systems for collecting waste at the surgical site typically include a suction source, tubing that extends from the suction source, and a container located between the tubing and the suction source. When the system is actuated, waste is drawn through the opening end of the tubing. The suction draws the waste through the tubing so that it flows into and is temporarily stored in the container. One exemplary system is the surgical waste collection system sold under the tradename NEPTUNE by Stryker Corporation (Kalamazoo, Mich.). Certain versions of the system include a mobile unit including a suction pump and at least one canister. The mobile unit provides for positioning the system in relatively close proximity to the patient, thereby reducing the extent to which the suction tubing, which invariably also functions as operating room clutter, interferes with surgical personnel. Further description of the features of certain versions of the systems are disclosed in commonly-owned U.S. Pat. Pub. No. 2007/0135779 and WO Pub. No. 2007/0760570, the contents of which are incorporated herein by reference in their entireties.

It is readily appreciated that collecting semisolid and solid waste entrained within the liquid waste is associated with technical challenges. A manifold may be provided that includes a filter element for trapping semisolid and solid waste entrained that may potentially clog the downline components of the medical/surgical waste system. Moreover, the manifold may be formed of a single use item, eliminating the need to sterilize the manifold and its intricate subcomponents. Consequently, personnel handling the used manifold only need to contact the outer surface of this component when disposing of it, thereby reducing or eliminating exposure of the personnel to the waste materials collected by the system.

Over time, the semisolid and solid waste entrained within the liquid waste may clog the filter element. The clogging of the filter element may result in an appreciable drop in the level of suction across the manifold, and likewise possibly result in a loss of suction at the surgical site. If complete loss of suction occurs, it may be necessary to interrupt the procedure and replace the manifold. Interrupting a surgical procedure runs contrary to a tenant of modern surgical practice of performing a procedure as quickly as possible so as to minimize the time the patient is held under anesthesia and limit exposure of normally concealed internal tissue to the open environment.

Therefore, a need exists in the art for a manifold for a medical/surgical waste collection system that overcomes one or more of the aforementioned disadvantages.

SUMMARY OF THE DISCLOSURE

This disclosure is directed to a new and useful manifold for use with a medical/surgical waste collection unit. The manifold of this disclosure is designed to accommodate relatively more amounts of semi-solid and solid waste material (also referred to as "material") entrained within the fluid. In one aspect the manifold reduces the amount of the material encountering the filter element, and in another aspect the manifold includes a greater capacity to accommodate the material once the filter element begins to clog. In both aspects, the manifold of the present disclosure reduces the likelihood that the manifold will clog over a given period of time, and likewise extends its operating life.

The manifold includes a housing with at least one sidewall defining a manifold volume, and a distal portion defining a distal end and including a longitudinal axis extending proximally from the distal end of the distal portion. An outlet opening is within a proximal portion of the housing and in fluid communication with the manifold volume. The manifold includes a filter element within the housing. The filter element includes a base, a mouth positioned opposite the base relative to the outlet opening, a basket extending between the base and the mouth, and porous features within the basket. At least one fitting defining a bore is in fluid communication with the manifold volume with the fitting adapted to receive a suction line for drawing fluid into the manifold volume. A fluid communication path is established from the bore of the fitting to the outlet opening through the manifold volume and across the filter element. The porous features are adapted to trap material entrained within the fluid as the fluid is drawn through the fluid communication path. A protrusion extends downwardly from the at least one sidewall to at least partially define a material collection volume within the housing. The material collection volume is located axially between the bore of the fitting and the mouth of the filter element, and further located opposite the basket of the filter element relative to the longitudinal axis. As the fluid and the material is drawn through the fluid communication path, the material collects within the material collection volume prior to encountering the mouth of the filter element.

The manifold may include a tissue trap defining the material collection volume. The tissue trap may be removably coupled to the housing with complementary coupling features to permit retrieval of the material collected within the material collection volume. The tissue trap may be substantially conical or pyramidal in shape. The tissue trap may be at least partially transparent and further comprises graduations for identifying a volume of the material collected within the tissue trap.

The filter element may include a snorkel coupled to the basket and at least partially located axially between the bore of the fitting and the mouth of the filter element. The snorkel defines a snorkel void space in fluid communication with the outlet opening and separated from a basket void space defined by the basket of the filter element. The filter element includes porous features within each of the basket and the snorkel. A second fluid communication path is established from the bore to the outlet opening through the snorkel void space of the snorkel. Suction is maintained through the second fluid communication path to draw the fluid through the second fluid communication path subsequent to substantially an entirety of the porous features of the basket being occluded with the trapped material and the material substantially occupying the basket void space.

The manifold may include a flow diverter within the housing and located axially between the bore of the fitting and the mouth of the filter element. The flow diverter is positioned within the fluid communication path. The flow diverter directs at least a portion of the fluid and the material being drawn through the fluid communication path towards the material collection volume. The flow diverter may include a baffle oriented at a non-right angle relative to the longitudinal axis of the manifold.

The basket of the filter element may be cylindrical and include an annular head extending from the cylindrical basket with the annular head. The annular head may be in the shape of a frustum of a cone and include porous features.

BRIEF DESCRIPTION OF THE DRAWINGS

Advantages of the present disclosure will be readily appreciated as the same becomes better understood by reference to the following detailed description when considered in connection with the accompanying drawings.

FIG. 6 is a perspective view of a proximal portion of the manifold of FIG. 4.

FIG. 7 is a perspective view of a distal portion of the manifold of FIG. 4.

FIG. 8 is a distal perspective view of a filter element shown in FIG. 2 and disposed within a housing of the manifold of FIG. 4.

FIG. 9 is a proximal perspective view of the filter element of FIG. 8.

FIG. 10 is a sectional view of the filter element of FIG. 2.

FIG. 12 is a perspective view of the manifold in accordance with another exemplary embodiment of the present disclosure.

FIG. 14 is a distal perspective view filter element shown in FIG. 13 and disposed within a housing of the manifold of FIG. 12.

FIG. 15 is a rear perspective view of the filter element of FIG. 14.

FIG. 16 is a distal plan view of the filter element of FIG. 14.

FIG. 17 is an elevation view of the manifold of FIG. 12 with a schematic representation of a material collection volume and a flow of waste through the manifold.

FIG. 22 is a distal perspective view of the flow diverter of FIG. 21.

FIG. 23 is a proximal perspective view of the flow diverter of FIG. 21.

DETAILED DESCRIPTION

Figure 1:
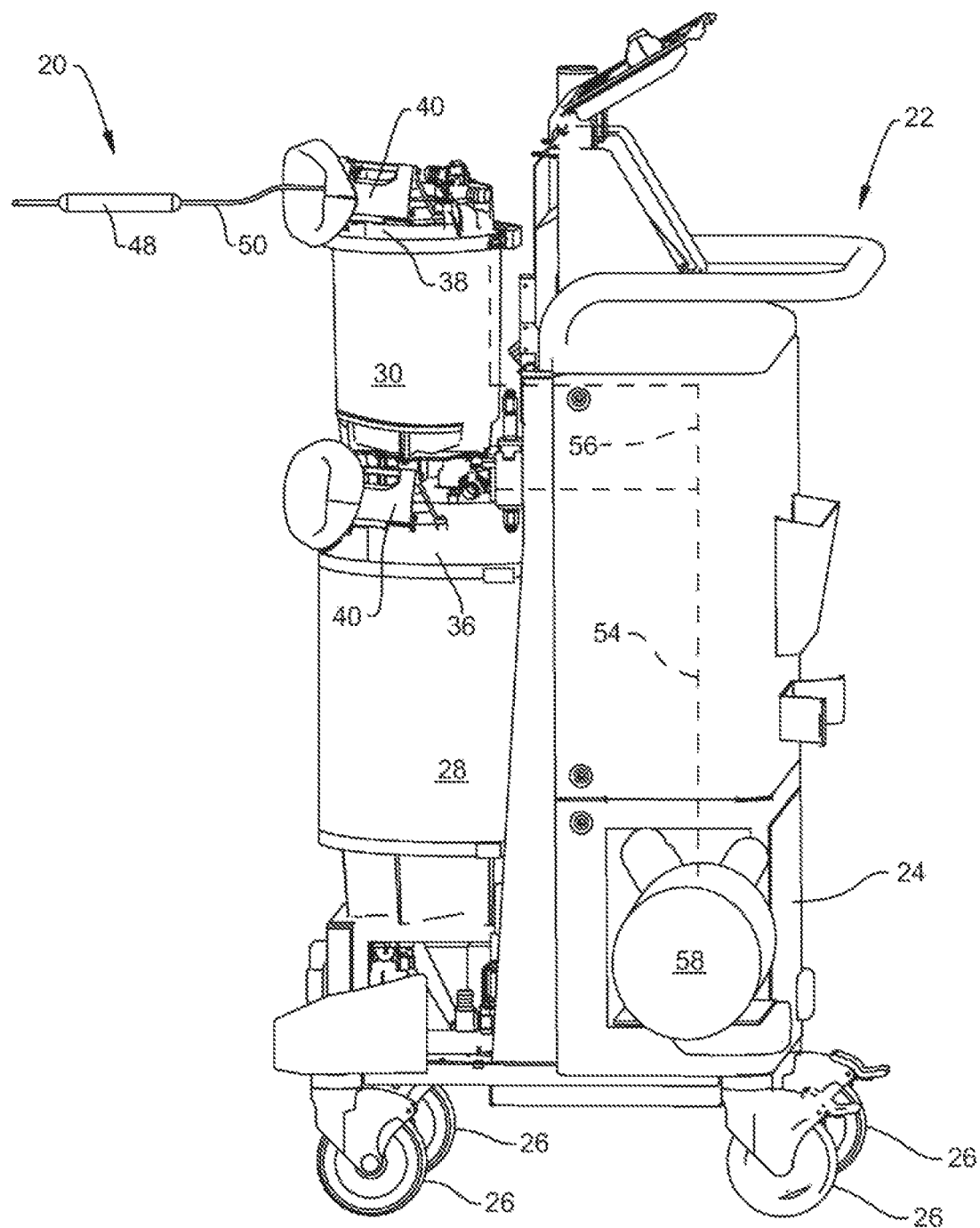
FIG. 1 depicts a medical/surgical waste collection system to which a manifold of this disclosure is coupled.

FIG. 1 illustrates a medical/surgical waste collection system 20. The waste collection system 20 may include a mobile unit 22 with a base 24 for supporting the mobile unit 22. Certain cover and door assemblies normally coupled to the base 24 are not present in FIG. 1 so the normally concealed components of the mobile unit 22 can be seen. Wheels 26 are attached to the bottom of the base 24 provide the waste collection system 20 with mobility, such as along a floor surface. Two canisters 28 and 30 are supported on the base 24. A first one of the canisters, canister 28, has a relatively large interior volume, for example, between approximately 10 and 40 liters. The second canister 30 is located above canister 28. The second canister 30 has a smaller volume, for example, between approximately 1 and 10 liters. In certain configurations, only one canister may be used.

Figure 2:
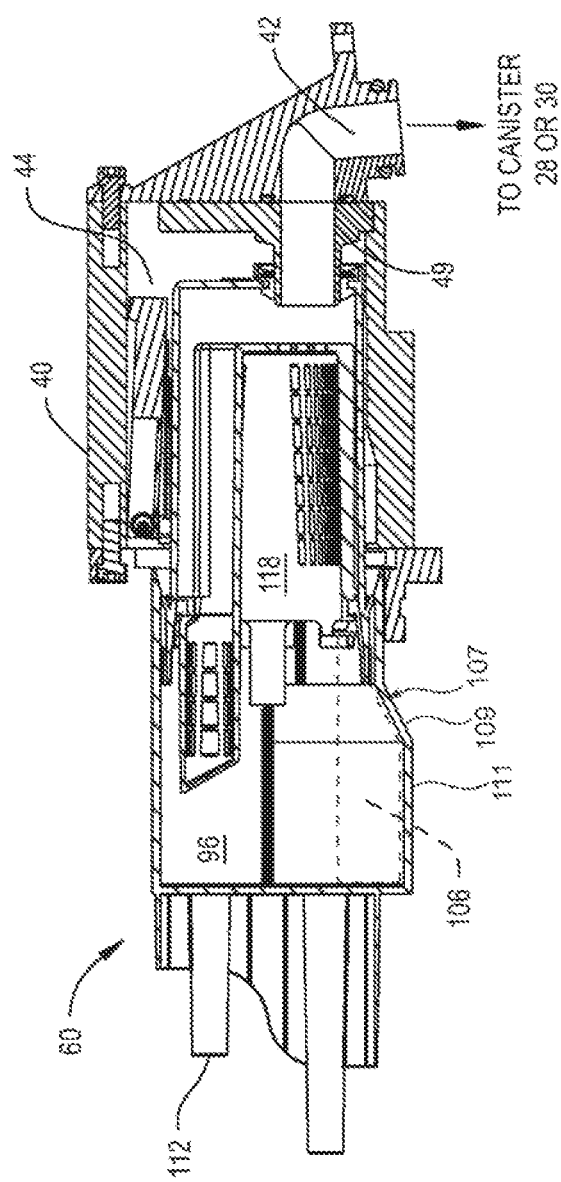
FIG. 2 illustrates in cross section a manifold in accordance with an exemplary embodiment of the present disclosure with the manifold seated in a manifold receiver of the medical/surgical waste collection unit.
Figure 3:
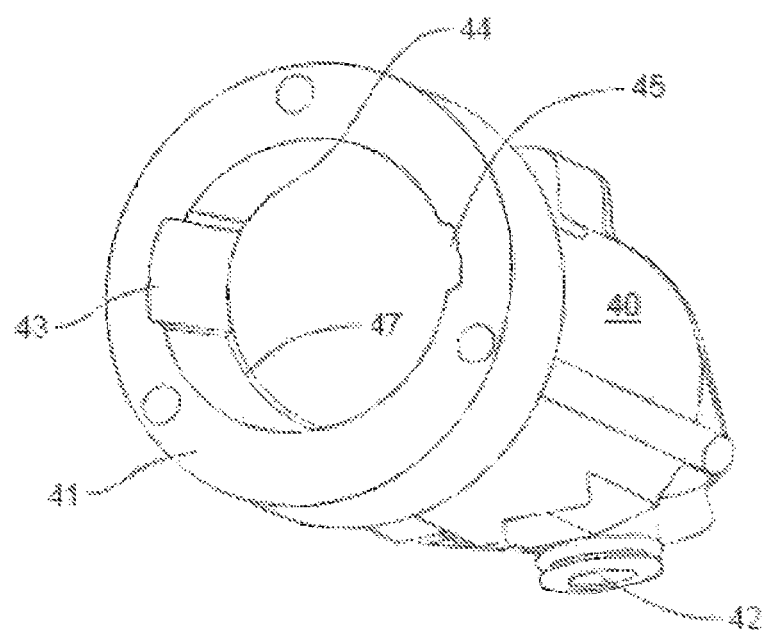
FIG. 3 is a perspective view of the manifold receiver of FIG. 2.

The waste collection system 20 includes a manifold receiver 40 coupled to upper portions 36, 38 of the canisters 28, 30. The manifold receiver 40 is configured to removably receive a manifold 60, 168, 242 to be described. In particular, each manifold receiver 40, best shown in FIGS. 2 and 3, is formed with a bore 44 that is closed at a proximal end and open at a distal end. Internal to the manifold receiver 40 is a fitting 49 that extends forward from the proximal end of the bore 44. A conduit 42 extends from the fitting 49 and establishes a fluid communication path from the manifold 60, 168, 242 into one of the canisters 28, 30 with which the manifold receiver 40 is associated.

Manifold receiver 40 may include a collar 41 defining the open distal end of bore 44 through which manifold 60, 168, 242 is inserted into the receiver 40. As shown in FIG. 3, the collar 41 is further formed to define two outwardly extending slots 43, 45. One of the slots 43 subtends a larger arc than the arc subtended by the other one of the slots 45. At the proximal end of each of the slots 43, 45 there is at least one groove 47. The groove(s) 47 extend outwardly from bore 44 between proximal ends of the slot 43, 45.

The manifold 60, 168, 242 is configured to receive at least one suction line 50 (shown in FIG. 1) in a manner to be described. A distal end of each suction line 50 is attached to a suction applicator 48. FIG. 1 shows the suction applicator 48 as a handpiece specifically and solely designed to apply suction. It is understood the suction applicator 48 may take on other forms, for example, as being incorporated into another surgical tool (e.g., an endoscope, ablation tool, etc.) applied to surgical site to accomplish a task in addition to applying suction.

The medical/surgical waste collection system 20 further includes a suction pump 58. Conduits 54, 56 (shown as dashed lines in FIG. 1) are in fluid communication with each of the canisters 28, 30 to the inlet port of the suction pump 58. When suction pump 58 is actuated, the resultant suction draws matter through the manifold 60, 168, 242 and manifold receiver 40, and into one or both of the canisters 28, 30. The waste material precipitates out of the stream into the canister(s) 28, 30, and the waste is stored until emptying. Gas, and in some instances bits of the waste material entrained in the gas, are directed towards the suction pump 58. Additional filters (not shown) may be within the fluid communication path to trap, for example, viral and bacterial-sized matter, prior to the stream being drawing into and exhausted out of the suction pump 58. As mentioned, aspects of the medical/surgical waste collection system 20, including description of the manifold receiver 40, is disclosed in commonly-owned U.S. Pat. Pub. No. 2007/0135779 and WO Pub. No. 2007/0760570, which are hereby incorporated by reference in their entirety.

I. First Embodiment

Figure 4:
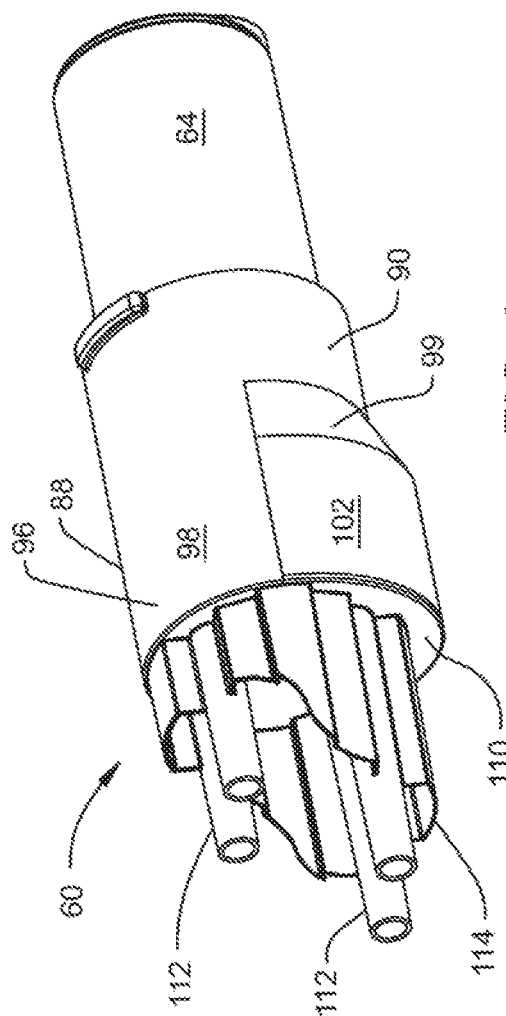
FIG. 4 is a perspective view of the manifold of FIG. 2.
Figure 5:
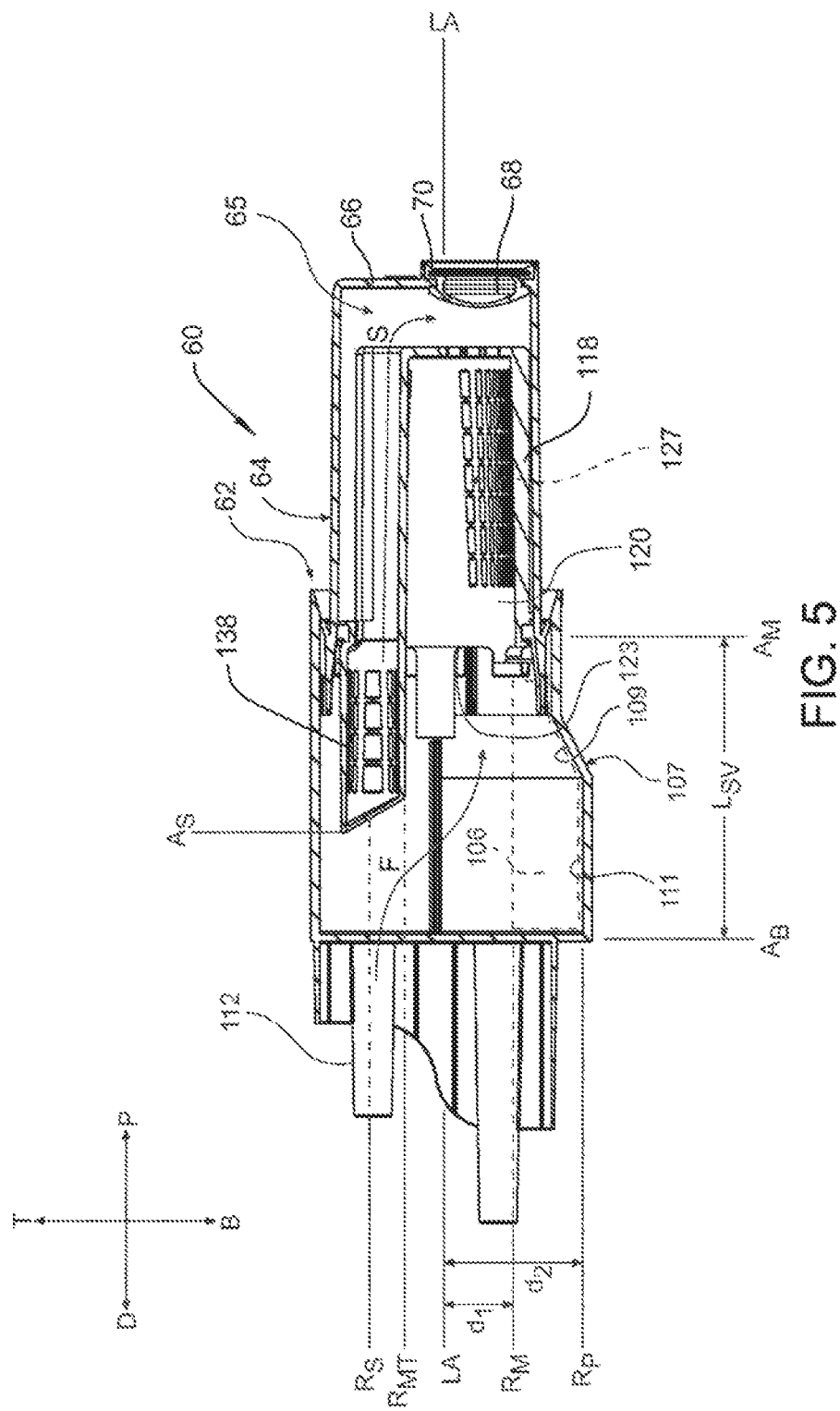
FIG. 5 is the cross sectional view of the manifold of FIG. 2 with the manifold receiver removed.

Referring now to FIGS. 2, 4 and 5, the manifold 60 includes a housing 62 with a distal portion 88 and a proximal portion 64. As used herein, "distal" (D) means towards the surgical site at which the suction is applied, and "proximal" (P) means away from the surgical site (see compass roses in FIGS. 5, 13 and 19). In other words, the proximal portion 64 and distal portion 88 form at least one sidewall of the housing 62 of the manifold 60. The sidewall of the housing 62 defines a manifold volume 65 of the manifold 60 to be described in greater detail. With further reference to FIGS. 6 and 7, the proximal portion 64 may be considered open-ended (when not coupled with the distal portion 88), and the distal portion 88 is configured to cover the open end of the proximal portion 64. The proximal portion 64 may be generally tubular or cylindrical in shape. The proximal portion 64 is dimensioned to seat in the bore 44 of the manifold receiver 40. The proximal portion 64 is further formed to have a base plate 66 defining a proximal end of the manifold 60. The manifold 60 includes an outlet opening 68 in fluid communication with the manifold volume 65 at, or adjacent to, the proximal end of the housing 62. In the illustrated embodiment, the base plate 66 is formed to define the outlet opening 68. The outlet opening 68 is dimensioned to receive the fitting 49 internal to the manifold receiver 40. A drip stop 70 may be disposed over outlet opening 68. When the manifold 60 is disconnected from the manifold receiver 40, the drip stop 70 prevents additional fluid flow out of the outlet opening 68.

With continued reference to FIGS. 6 and 7, a number of arcuately spaced apart tabs 72 may extend distally forward from the distal end of the proximal portion 64 (three tabs identified in FIG. 6). Some of tabs 72 may subtend different arcs relative to the other tabs, and some of the tabs 72 may have different arcuate lengths. The tabs 72 facilitate alignment and securement of proximal portion 64 to the distal portion 88. The proximal portion 64 is also formed to have a lip 74 that extends radially outward from an outer surface of the proximal portion 64. The lip 74 is typically located one centimeter or less from the distal end of the proximal portion 64. The distal portion 88 may include a tube like neck 90 dimensioned to seat over the distal end of the proximal portion 64. A number of ribs 92 may extend inwardly from the inner surface of the neck 90 (two ribs identified in FIG. 7). Collectively, the tabs 72 and the ribs 92 are arranged to ensure that when the proximal portion 64 is inserted in the neck 90, the proximal portion 64 is in the correct rotational alignment with the distal portion 88. The proximal portion 64 and neck 90 are further dimensioned so that, when the proximal portion 64 is inserted in the neck 90, the lip 74 abuts an inner wall of the distal portion 88 to minimize leakage between the proximal portion 64 and distal portion 88. The distal portion 88 may also include tabs 95, 97 projecting radially outwardly from an outer surface of the neck 90. The tabs 95, 97 extend outwardly from a location immediately forward of the proximal end of the neck 90. The tabs 95, 97 may subtend arcs of different lengths. One of the tabs 95 is dimensioned to seat in one slot 43, and the other one of the tabs 97 is dimensioned to seat in the other slot 45. The tabs 95, 97 are further dimensioned to rotate in the grooves 47 that extend arcuately from the proximal ends of the slots 43, 45. The seating of tabs 95, 97 in the slots 43, 45, facilitates the manifold 60 having the proper rotation orientation within the bore 44 when the manifold 60 is seated in the manifold receiver 40. The tabs may be omitted in certain configurations or may take other forms than that explicitly described above.

FIG. 4 shows the distal portion 88 is shaped to include a head 96 distal to the neck 90. The head 96 may optionally include an upper section 98 and a lower section 102 with the upper section 98 being an extension of the neck 90. In other words, the upper section 98 has the same radius of curvature of the neck 90 and generally appears as a continuous structure. The lower section 102 is below the upper section 98 and protrudes outwardly from the adjacent portion of the neck 90. In the illustrated embodiment, a transition panel 99 may extend between the lower section 102 and the adjacent portion of the neck 90. The transition panel 99 may at least partially define a protrusion 107 of the manifold 60 to be described.

The distal section 88 of the manifold 60 may include a face plate 110 defining a distal end of the manifold 60. The manifold 60 includes at least one fitting 112 at the distal end with the fitting(s) 112 adapted to receive the suction line(s) 50. In the illustrated embodiment, the manifold 60 includes four fittings 112. The fitting(s) 112 may extend distally from the face plate 110. The fittings 112 define a bore in fluid communication with the manifold volume 65, and more particularly, the bore opens into the manifold volume 65 immediately proximal to the face plate 110. With the suction lines 50 coupled to the fittings 112, material and fluid may be drawn from the surgical site into the manifold volume 65. The manifold 60 may further include fence panels 114 extending forward from the face plate 110. The fence panels 114 are a series of rectangular stepped wall-like structures that function as finger holds that allow the manifold 60 to be manipulated when initially positioned within the manifold receiver 40. The fittings 112 extend distally forward of the fence panels 114.

A filter element 118, now described with reference to FIGS. 5 and 8-10 is disposed within the housing 62. The filter element 118 may be removably coupled to the housing 62. The filter element 118 may include a basket 120 defined between a base 122 that forms a proximal end of the filter element 118, and a mouth 123 that forms a distal end of the filter element 118. In the illustrated embodiment, the basket 120 is generally, but not entirely, cylindrical in shape to form a tubular sleeve 124 extending between the base 122 and the mouth 123. When situated within the housing 62, at least a portion of the sleeve 124 including the base 122 is positioned within the proximal portion 64. In certain embodiments, the filter element 118 includes one or more ribs 128 that protrude outwardly or radially from an outer surface of the sleeve 124. The ribs 128 extend longitudinally along the outer surface of the sleeve 124 and are sized to an inner diameter of the proximal portion 64 such that the ribs 128 radially align and support the filter element 118 within the housing 62. Rotational alignment between the filter element 118 and the housing 62 is facilitated with tabs 130 that project outwardly near the mouth 123 of the sleeve 124. The filter element 118 may be constructed with two pairs of tabs 130, as illustrated in FIG. 8, with each of the pairs on parallel axes. The tabs 130 are adapted to be seated between the ribs 92 integral with proximal portion 64 (see FIG. 7) to prevent rotation of filter element 118 relative to the proximal portion 64. The filter element 118 may further include additional tabs 134 extending distally forward from the mouth 123 of the sleeve 124. The tabs 134 may be L-shaped, and may subtend different arcs around the circumference of the circle defined by basket 120. A distal portion of each of the tabs 134 extends radially outwardly from a proximal portion that extends axially distally to the sleeve 124. The tabs 134 are configured to be sealed between the ribs 92 internal to the distal portion 88 (see FIG. 7). The ribs 92 and the tabs 134 are collectively formed such that, when the manifold 60 is assembled, the basket 120 is in the proper angular orientation relative the manifold volume 65 within the proximal portion 64 and a material collection volume 106 within the distal portion 88 to be described. The filter element 118 may be further formed so as to define a groove 126 that extends circumferentially around the sleeve 124 near the mouth 123. The groove 126 is adapted to receive a seal (not shown), such as an O-ring, to provide a sealing interface between the filter element 118 and the housing 62 and direct substantially an entirety of the fluid stream through the filter element 118. In certain embodiments, the filter element 118 is constructed as a single-piece component.

As mentioned, the filter element 118 includes the basket 120 defined between the base 122 and the mouth 123 to form the sleeve 124 extending between the base 122 and the mouth 123. The filter element 118 includes porous features 142 within the basket 120, and more particularly within the base 122 and the sleeve 124 of the basket 120. The porous features 142 may be provided any suitable quantity, size, shape, and/or arrangement. FIGS. 8-10, for example, show the porous features 142 generally rectangular in shape and arranged in a rectangular array on the sleeve 124, and in a radial array on the base 122. The porous features 142 are generally sized so as trap material entrained within the fluid as the fluid is drawn across the filter element 118. With the filter element 118 disposed within the housing 62 and the suction line 50 coupled to the fitting 112, a fluid communication path is established from the bore of the fitting 112 to the outlet opening 68 through the manifold volume 65 and across the filter element 118. The porous features 142 trap the material entrained within the fluid as the fluid is drawn through the fluid communication path. With extended or repeated use over time, the porous features 142 of the filter element 118 may partially or completely clog with the semi-solid and solid matter entrained within the fluid possibly resulting in a drop in suction across the manifold and/or at the surgical site. Owing to the disposability of the manifold 60, one option includes removing and replacing the manifold 60, as previously described. However, further advantageous features of the manifold 60 of the present disclosure provide for reducing the likelihood that the manifold 60 will clog over a given period time, thereby extending the operating life of the manifold 60.

Figure 11:
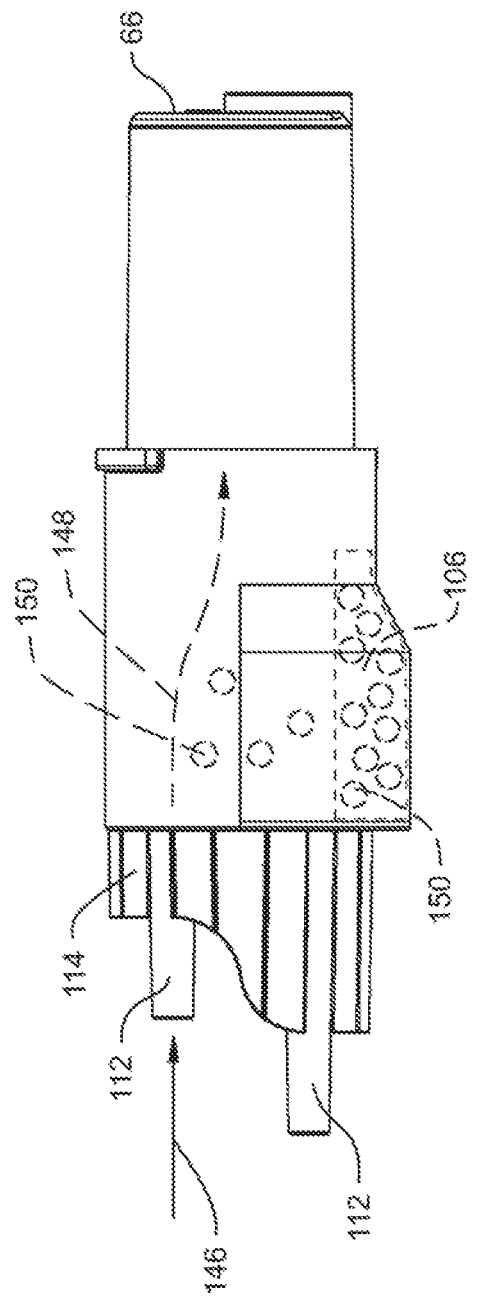
FIG. 11 is an elevation view of the manifold of FIG. 4 with a schematic representation of a material collection volume and a flow of waste through the manifold.

Referring now to FIGS. 2, 5 and 11, the manifold 60 includes a material collection volume 106. In a most general sense, the material collection volume 106 is a volume suitably sized and positioned within the housing 62 such that material 150 (e.g., bits of semisolid and/or solid matter represented by dashed circles) deposits and collects within the volume 106. The manifold 60 of the present disclosure is configured to accommodate more material within the fluid path prior to requiring replacement. The manifold 60 may be considered a large capacity manifold. This may be accomplished in at least two ways. First, once the porous features 142 of the filter element 118 begin clogging with the material entrained within the fluid, an initial buildup of the material is near the base 122 of the filter element 118 based on the presence of suction, followed by continued accumulation of the material along a length of the filter element 118. Owing to the force of gravity, the material may initially accumulate along a bottom of the length of the filter element 118. Likewise, additional material 150 is collected within the material collection volume 106 near the bottom of the manifold 60 as opposed to, for example, further accumulating within the filter element 118. Second, based on the position and size of the material collection volume 106 to be described, the density of the material 150 relative to the fluid may result in at least some of the material 150 descending towards and collecting within the material collection volume 106 prior to encountering the mouth 123 of the filter element 118. With the material 150 collected and settled within the material collection volume 106, less solid or semi-solid material enters the filter element 118 to potentially occlude the porous features 142.

With particular reference to FIG. 5, the material collection volume 106 will now be described in detail. The distal portion 88 of the manifold 60 may include a longitudinal axis LA extending proximally from the distal end, for example the face plate 110, of the distal portion 88. In embodiments where the manifold 60 is substantially cylindrical, the longitudinal axis LA may be at a radial center of the manifold 60. In other embodiments where an axial cross section of the manifold 60 is not substantially circular, the longitudinal axis LA may be at a geometric center of the cross section. It is to be understood that the longitudinal axis LA may be approximated at a middle of the manifold 60 and its precise location may be defined with some variance. The longitudinal axis LA, when the manifold 60 is coupled to the medical-surgical waste system 20, may be substantially horizontal and extending proximally (P) to distally (P) to define a top direction (T) and a bottom direction (B) in the convention shown in FIG. 5.

The material collection volume 106 is located below a bottom of the basket 120 of the filter element 118 relative to horizontal (i.e., in the bottom direction). In other words, the material collection volume 106 is located opposite the basket 120 of the filter element 118 relative to the longitudinal axis LA. With the material collection volume 106 below the bottom of the basket 120, the material 150 collected with the material collection volume 106 is effectively removed from the fluid communication path. The suction forces may be insufficient to draw the solid and semi-solid waste material from within the material collection volume 106 positioned below the basket 120 into the fluid communication path. The manifold volume 65 may be considered the volume within the housing 62 other than the material collection volume 106, or alternatively the material collection volume 106 may be considered a sub-volume of the manifold volume 65 defined by the housing 62.

The material collection volume 106 is defined by a protrusion 107 extending downwardly (i.e., in the bottom direction) from the sidewall of the housing 62, and more particularly the neck 90 of the distal portion 88. The protrusion 107 may be considered to extend downwardly from the sidewall relative to a portion of the sidewall proximal to the protrusion 107. The protrusion 107 extends downwardly relative to horizontal. As mentioned, at least a portion of the protrusion 107 may be defined by the transition panel 99 separating the lower section 102 from the neck 90 of the distal portion 88 (see FIG. 4). In the exemplary embodiment illustrated in FIG. 5, the protrusion 107 includes a first surface 109 and a second surface 111 with the first surface 109 extending downwardly from the sidewall of the housing 62. The second surface 111 extends distally from the first surface 109 to the face plate 110 defining the distal end of the housing 62. In such an embodiment, the material collection volume 106 may be at least partially defined by the first and second surfaces 109, 111 and a portion of the face plate 110. FIG. 5 shows that the bottom of the basket 120 is defined on an axis, $R_M$ (radial axis of mouth 123), at a first distance, $d_1$, from the longitudinal axis LA. The protrusion 107, and more particularly a bottommost portion of the protrusion 107 (e.g., the second surface 111) is at a second distance, $d_2$, from the longitudinal axis LA. The second distance is greater than the first distance with the difference defining a depth of the material collection volume 106. In another convention, the depth of the material collection volume 106 is defined between a first distance from the longitudinal axis LA to the sidewall of the housing 62 and the second distance, $d_2$, from the longitudinal axis LA to the bottommost portion of the protrusion 107 (i.e., a depth of the protrusion 107). The depth of the material collection volume 106 may be configured to provide sufficient capacity for the material 150, for example, at least 5 millimeters (mm), at least 10 mm, at least 20 mm, at least 50 mm, or at least 100 or more millimeters. Alternatively, the depth of the material collection volume 106 may range from 5 to 100 mm, 10 to 75 mm, or 20 to 50 mm. It is understood, however, that the depth of the material collection volume 106, may be designed based on the dimensional constraints of the housing 62 and/or the needs of the surgical application. The volume of the material collection volume 106 may be at least 5, 6, 7, 8, 9, or 10 cubic centimeters (cm³). Alternatively, the volume of the material collection volume 106 may range from 1 to 10, 3 to 8, or 4 to 6 cm³. In certain embodiments, the ratio of the volume of the material collection volume 106 to the manifold volume 65 ranges from 1:3 to 1:8, from 1:3 to 1:6, or from 1:4 to 1:5. Alternatively, the manifold volume 65 may be at least 2, 3, 4, 5, or 6 times the volume of the material collection volume 106.

The material collection volume 106 is located at least partially distal to the filter element 118. More specifically, the material collection volume 106 is at least partially located distal to the mouth 123 of the filter element 118, and even more specifically, axially between a proximal end of the bore of the fitting 112 and the mouth 123 of the filter element 118. With the material collection volume 106 distal to the mouth 123, the material 150 descends and collects with the material collection volume 106 prior to encountering the mouth 123 of the filter element 118. FIG. 5 shows that the mouth 123 is defined at axis, $A_M$ (axial position of the mouth 123), and a proximal end of the bore of the fitting 112 is defined at an axis, $A_B$ (axial position of the bore). If the bore terminates at the face plate 110, as shown in FIG. 5, the axis $A_B$ correspond to the face plate 110. A length of the material collection volume 106, $L_{SV}$, may be defined between the axes $A_B$, $A_M$. The length may be within the range of 25 to 250 mm, within the range of 50 to 125 mm, within the range of 25 to 75 mm, or within the range of 15 to 50 mm. The length may be designed to permit the density of the material 150 relative to the fluid to result in the material 150 descending out of the fluid communication path to collect within the material collection volume 106. It is understood that the length may be designed based on, for example, the anticipated levels of suction for the surgical applications, as higher levels of suction will draw the semi-solid and solid material with greater force and require more distance for the semi-solid and solid material to descend from the fluid path under the force of gravity. The material collection volume 106 may be trapezoidal when viewed in the sectional elevation view of FIG. 5, but it is contemplated that the protrusion 107 may define the material collection volume 106 to be rectangular, semicircular, triangular, other polygonal shapes, and/or any shape defining a continuations surface.

It should be readily appreciated that with much of the semi-solid and solid material collecting within the material collection volume 106, the manifold 60 of the present disclosure is configured to accommodate more material prior to requiring replacement. Even with this robust feature, eventually the material collection volume 106 will be consumed with the material 150 and the porous features 142 of the filter element 118 will ultimately become occluded. As the manifold volume 65 begins to accumulate more and more material, a further advantageous feature of the manifold 60 of the present disclosure includes a snorkel 138 designed to define a snorkel void space 129 (see FIG. 10) inaccessible to the material 150 and provide a second fluid communication path to be described.

Referring to FIGS. 5 and 8-10, the snorkel 138 is shown as a component or portion of the filter element 118. However, it should be appreciated that the snorkel 138 may be a distinct component. The snorkel 138 extends distally from the basket 120, and more particularly, from the mouth 123 of the filter element 118. In other words, the mouth 123 of the filter element 118 may define a filter mouth plane (sec, for example, a plane on the axis $A_M$ of FIG. 5) with the snorkel 138 extending distally from the plane FIG. 8 shows the basket 120 extending proximally from the filter mouth plane. The snorkel 138 is positioned within the housing 62, and more particularly within the distal portion 88 of the housing 62. The snorkel 138 coupled to the basket 120 is at least partially located axially between a proximal end of the bore of the fitting 112 and the mouth 123 of the filter element 118. Further, FIG. 5 shows the snorkel 138 being oriented and located on an axis, $R_S$ (radial axis of snorkel 138). The axis $R_S$ of the snorkel 138 is opposite to the material collection volume 106 relative to the longitudinal axis LA. In other words, whereas the material collection volume 106 is generally located near a bottom of the manifold 60, the snorkel 138 is generally located near a top of the same. In certain embodiments, such as the one illustrated in FIG. 5, the snorkel 138 is positioned above the material collection volume 106. It is further indicated in FIG. 5 that the top of the basket 120 is defined on an axis, $R_{MT}$ (radial axis of mouth 123) with the axis $R_S$ of the snorkel 138 being above the axis $R_{MT}$ of the top of the basket 120. For reason to be described, the snorkel 138 is advantageously positioned near the distalmost and uppermost portion of the manifold 60 remote from the outlet opening 68. It should be appreciated that the snorkel 138 may be included in the manifold 60 without inclusion of the material collection volume 106.

In certain embodiments, the snorkel 138 is a generally tubular structure. For example, the snorkel 138 includes a tubular wall 141, and a distal face 140 at a distal end of the tubular wall 141. The snorkel 138 includes the porous features 142, which may be the same or similar to the porous features 142 associated with the basket 120, disposed on one or both of the tubular wall 141 and the distal face 140. The snorkel 138 may not include a proximal face opposite the distal face 140 such that the snorkel 138 is generally concave relative to the mouth 123 of the filter element 118. It is noted that the basket 120 of the filter element 118 may be considered generally convex relative to the mouth 123 of the filter element 118. Rather than a proximal face, the snorkel 138 opens into a channel defined by a groove 125 of the sleeve 124, as best shown in FIG. 9. The groove 125 may be generally U-shaped or semi-circular and subtend an arc corresponding to a portion of the tubular wall 141 (i.e., the groove 125 is flush with the adjacent curved section of the snorkel 138).

With particular reference to FIG. 10, the basket 120 may define a basket void space 127 interior to the sleeve 124 between the base 122 and the mouth 123. The mouth 123 is opened such that the basket void space 127 is opened towards the inner, proximally directed surface of face plate 110. The snorkel 138 may define the snorkel void space 129 interior to the tubular wall 141 between the distal face 140 and a proximal end of the wall 141. It is appreciated that the snorkel void space 129 is separate from the basket void space 127. In particular, the tubular wall 141 of the snorkel 138 and the groove 125 may separate the snorkel void space 129 from the basket void space 127. The structure of the filter element 118, including the basket 120 and the snorkel 138, establishes the first fluid communication path (F) previously described (see also FIG. 5), and a second fluid communication path (S) from the bore of the fitting 112 to the outlet opening through the snorkel void space 129 of the snorkel 138. More particularly, the second fluid communication path includes fluid traveling from the bore of the fitting 112, through the porous features 142 of the snorkel 138, through the snorkel void space 129, through the channel defined by the groove 125, and descending near the base 122 of the basket 120 to the outlet opening 68. Thus, subsequent to substantially an entirety of the porous features 142 of the basket 120 being occluded with the trapped material 150 and the material 150 substantially occupying the basket void space 127, suction is maintained through the second fluid communication path to draw the fluid through the second fluid communication path. The material entrained within the fluid path is prevented from entering the snorkel void space 129 with the porous features 142 on the snorkel 138. Further, with the axial and radial position of the snorkel 138 being near the farthest-most portion of the manifold volume 65 from the outlet opening 68, the manifold 60 should continue to operate until substantially an entirety of the volume within the housing 62 is consumed with semi-solid and solid material. Only then is it more likely that the material will clog the porous feature 142 of the snorkel 138 at the distalmost and uppermost portion of the manifold 60. As a result, substantially an entirety of the volume within the manifold 60 is utilized, extending the operating life of the manifold 60.

An exemplary operation includes the waste collection unit 20 being prepared for use by inserting the manifold 60 within the manifold receiver 40. The manifold 60 is rotated so as to seat the tabs 95, 97 within the grooves integral with slots 43, 45 to releasably lock the manifold 60 in the manifold receiver 40. Owing to how the manifold 60 is oriented when coupled with the manifold receiver 40, in terms of the gravity plane of reference, the material collection volume 106 is located below the filter element 118. At least one suction line 50 is coupled to at least one of the fittings 112. The suction applicator 48 may be coupled to the suction line 50.

The pump 58 is actuated to draw waste away from the surgical site. The actuation of the pump draws a waste stream through the suction applicator 48 and suction line 50 into the manifold 60, represented by arrow 146 in FIG. 11. Based on the position of the material collection volume 106, the fluid stream with the material 150 does not immediately encounter the filter element 118. Rather, the fluid stream with the material 150 travels through the first communication path, represented by arrow 148 in FIG. 11 (see also (F) in FIG. 5). At least some of the material 150 may descend towards and collect within the material collection volume 106 prior to encountering the mouth 123 of the filter element 118. The fluid is drawn into one of the canisters 28, 30 in fluid communication with the manifold volume 65. Further, subsequent to at least some of the porous features 142 of the filter element 118 clogging with the material 150 entrained within the fluid, the material 150 collects within the material collection volume 106 near the bottom of the manifold 60 as opposed to, for example, further accumulating within the filter element 118.

II. Second Embodiment

Figure 13:
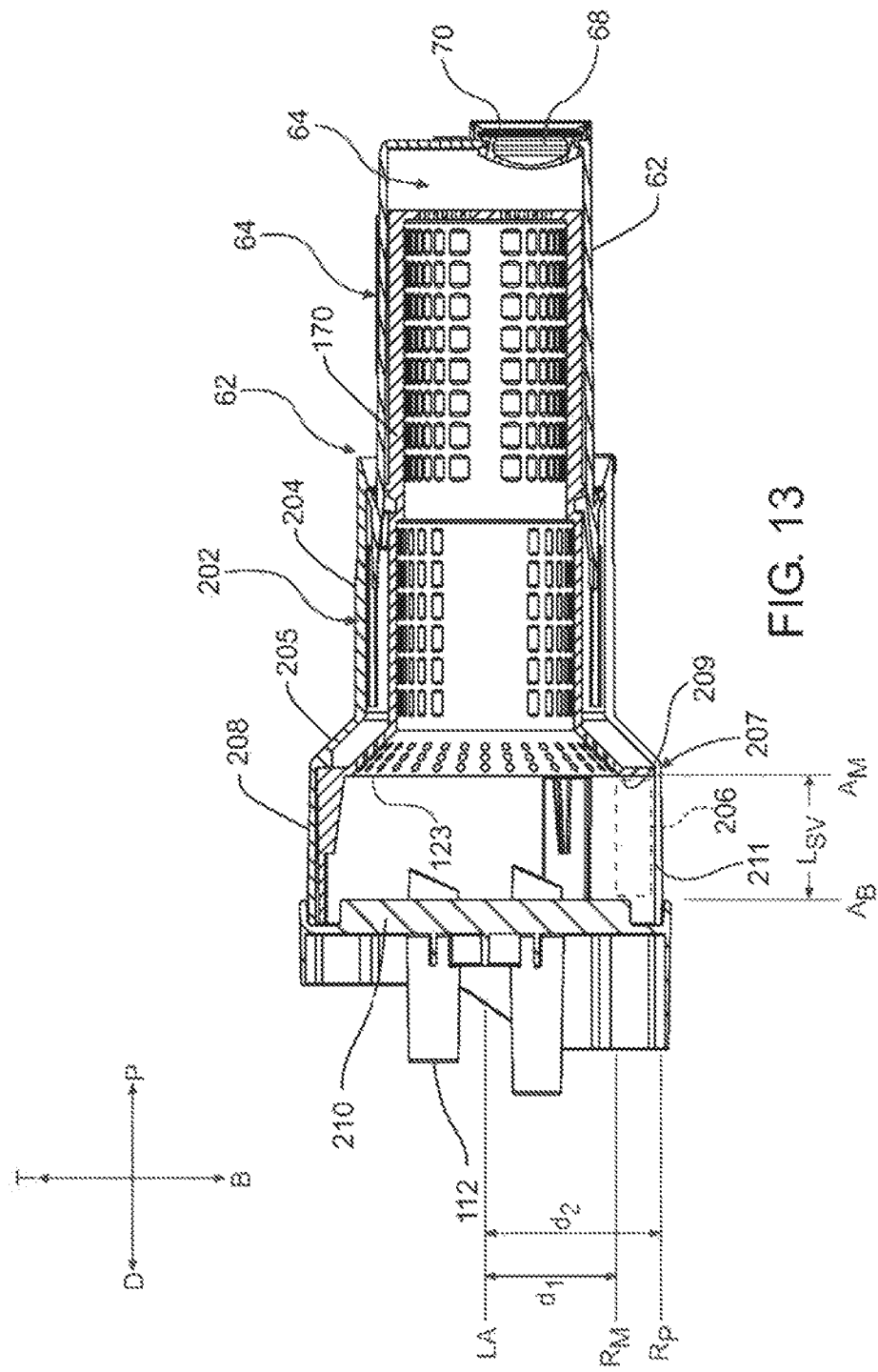
FIG. 13 is a sectional view of the manifold of FIG. 12.

FIGS. 12, 13 and 17 show a manifold 168 in accordance with another exemplary embodiment of the present disclosure. Similarly numbered structures from the previously described embodiment of the manifold 60 are herein incorporated by reference for the present embodiment of the manifold 168 to be described. The manifold 168 includes the proximal portion 64 and a distal portion 202. The distal portion 202 may be removably coupled to the proximal portion 64, such as with snap-fittings, detents, and the like. The proximal and distal portions 64, 202 collectively define the housing 62 of the manifold 168. The distal portion 202 is similar in many respects to the distal portion 88 with exceptions of its comparative shape and dimensions. In particular, a neck 204 of the distal portion 202 is axially longer than the neck 90 of the distal portion 88 of FIG. 4. The neck 204 of the distal portion 202 of the present embodiment is cylindrical along its entire length. Further, the distal portion 202 includes a collar 205 annularly flaring radially outwardly from the neck 204. In at least some respects the collar 205 is similar to the transition panel 99 previously described with the collar 205 at least partially defining the protrusion 207. Distal to the collar 205, the distal portion 202 of the housing 62 includes a head 208 having a diameter greater than that of the neck 204. The manifold 168 includes a face plate 210 defining a distal end of the manifold 168. The fittings 112 and fence section 114 extend forward from face plate 210. The fittings 112 define the bore in communication with the manifold volume 65 within the manifold 168. In certain embodiments, the manifold 168 includes blisters 203 protruding radially outwardly from the otherwise cylindrical surface of the neck 204. In the illustrated embodiment, the blisters 203 are diametrically opposed. The blisters 203 are adapted to provide a friction fit between the manifold 168 and the collar 41 of the manifold receiver 40. In one example, the neck 204 of the manifold 168 is sized with a diameter approximately 0.5 mm less than the diameter of the collar 41, and the blisters 203 protrude radially outwardly to a distance of approximately 0.05 mm more than the diameter of the manifold receiver 40. The blisters 203 may be formed from resilient material adapted to compress and resiliently deform when the manifold 168 is positioned within the manifold receiver 40. The compression and associated resilient deformation facilitates preventing rotation of the manifold 168 relative to the medical/surgical waste collection system 20.

Referring now to FIGS. 14-16, the filter element 170 includes a basket 174. The basket 174 is substantially cylindrical. The basket 174 extends between a base 172 defining a proximal end of the filter element 170, and a mouth 123 opposite the base 172 defining a distal end of the filter element 170. The basket 174 is sized and shaped to be positioned within the housing 62. A neck 182 is distal to the basket 174 with the neck 182 having an inner diameter that is approximately three millimeters greater than the inner diameter of the basket 174. The filter element 170 includes a head 184 extending distally from the neck 182. The head 184 is annularly shaped like the frustum of a cone. In other words, the head 184 flares or tapers radially outwardly from the neck 182. A ring-shaped rim 188, also part of the head 184, extends radially outwardly from the outer perimeter of the head 184. The rim 188 is planar in shape and defines the mouth 123 of the filter element 170. The rim 188 has an outer diameter approximately one millimeter less than the diameter of the inner wall of the head 208 of distal portion 202. However, it should be appreciated that the filter basket 174 may have other shapes as well.

The filter element 170 includes ribs 176, bumps 178, and ears 190 configured to maintain the position of the filter element 170 relative to the housing 62. More particularly, the ribs 176 may extend radially outwardly from an outer surface of the basket 174. The ribs 176 may be oriented longitudinally along the outer surface of the basket 174. FIGS. 14 and 15 show four ribs 176 angularly spaced equally about a circumference defined by the outer surface of the basket 174. The ribs 176 are sized such that the basket 174 is snugly received within the proximal portion 64 of the housing 62, and further sized such that a gap of a desired size is provided between the outer surface of the basket 174 and an inner surface of the proximal portion 64. The gap provides clearance for the fluid passing through porous features 194 (described further below) of the filter element 170. The bumps 178 facilitate centering the filter element 170 within the proximal portion 64 of the housing 62. As shown in FIGS. 14 and 15, the bumps 178 project outwardly from each of the ribs 176, and more specifically at a distal end of each of the ribs. The bumps 178 are sized such that, when the filter element 170 is seated within the housing 62, the bumps 178 abut the inner surface of the proximal portion 64. The ears 190 extend distally forward from the rim 188. In one example, each of the ears 190 is in the form of a curved tab. When manifold 168 is assembled, the ears 190 are disposed between ribs (not shown) protruding inwardly from the inner surface of head 208. The seating of the ears 190 between the ribs facilitates the alignment of the filter element 170 in the manifold 168 to prevent rotation of the filter.

The filter element 170 includes porous features 194. The porous features 194 may be disposed within the base 172, the basket 174, the neck 182, and/or head 184. FIGS. 14-16 show no porous features associated with the rim 188. The porous features 194 are generally sized so as to trap material entrained within the fluid as the fluid is drawn across the filter element 170. With the filter element 170 disposed within the housing 62 and the suction line 50 coupled to the fitting 12, a fluid communication path is established from the bore of the fitting 112 to the outlet opening 68 through the manifold volume 65 and across the filter element 170. The porous features 194 trap the material 150 entrained within the fluid as the fluid is drawn through the fluid communication path. With extended or repeated use over time, the porous features 194 of the filter element 118 may partially or completely clog with the semi-solid and solid matter entrained within the fluid, possibly resulting in drop in suction across the manifold 168 and/or at the surgical site. The present embodiment of the manifold 168 includes a material collection volume 206 in many respects similar to the material collection volume 106 of the exemplary embodiment previously described (see FIG. 5). In a most general sense, the material collection volume 206 a volume suitably sized and positioned within the housing 62 such that the material 150 deposits and collects within the material collection volume 206.

With reference to FIG. 13, the distal portion 202 of the manifold 168 includes the longitudinal axis LA extending proximally from the distal end of the distal portion 202 and oriented proximally (P) to distally (P) to define a top direction (T) and a direction (B). The material collection volume 206 is located below a bottom of the basket 174 of the filter element 170 relative to horizontal. In other words, the material collection volume 206 is located opposite the basket 174 of the filter element 170 relative to the longitudinal axis LA. With the material collection volume 206 below the bottom of the basket 174, the material 150 descending into and collecting with the material collection volume 206 is effectively removed from the fluid communication path. The material collection volume 206 is defined by the protrusion 207 extending downwardly from the sidewall of the housing 62. The protrusion 207 may be at least partially defined by the collar 205 and/or the head 208 of the proximal portion 202. In the present embodiment, the rim 188 of the filter element 170 may be considered to comprise a first surface 209 defining a portion of the material collection volume 206, a second surface 211 extends proximally from the face plate 210 defining the distal end of the housing 62. In such an embodiment, the material collection volume 206 may be at least partially defined by the first and second surface 209, 211 and a portion attic face plate 210, as represented by the dashed rectangle in FIG. 13. FIG. 13 further shows that the bottom of the basket 174 is defined on the axis, $R_M$, at the first distance, $d_1$, from the longitudinal axis LA, and the protrusion 207, and more particularly a bottom of the protrusion 207 (e.g., the second surface 211) is at the second distance, $d_2$, from the longitudinal axis LA. The second distance is greater than the first distance with the difference defining a depth of the material collection volume 206 in another convention, the depth of the material collection volume 206 is defined between a first distance from the longitudinal axis LA to the sidewall of the housing 62 proximal to the protrusion 207, and the second distance, $d_2$, from the longitudinal axis LA to the bottommost portion of the protrusion 207 (i.e., a depth of the protrusion 207). The depth of the material collection volume 206 may be configured to provide sufficient capacity for the material 150, for example, at least 5 mm, least 10 mm at least 20 mm, at least 50 mm, or at least 100 or more millimeters. Alternatively, the depth of the material collection volume 206, may range from 5 to 100 mm, 10 to 75 mm, or 2.0 to 50 mm. It is understood, however, that the depth of the material collection volume 206, may be designed based on the dimensional constraints of the housing 62 and/or the needs of the surgical application. The volume of the material collection volume 206 may be at least 5, 6, 7, 8, 9, or 10 cm$^3$. Alternatively, the volume of the material collection volume 206 may range from 1 to 10, 3 to 8, of 4 to 6 cm$^3$. In certain embodiments, the ratio of the volume of the material collection volume 206 to the manifold volume 65 ranges from 1:3 to 1:8, from 1:3 to 1:6, or from 1:4 to 1:5. Alternatively, the manifold volume 65 may be at least 2, 3, 4, 5, or 6 times the volume of the material collection volume 206.

The material collection volume 206 is located at least partially distal to the filter element 170. More specifically, the material collection volume 206 is located distally to the mouth 123 of the filter element 170, and even more specifically, axially between the face plate 210 and the mouth 123 of the filter element 170. The material collection volume 206 may be axially between a proximal end of the bore of the fitting 112 and the mouth 123 of the filter element 170. With the material collection volume 206 distal to the mouth 123, the material 150 descends and collects within the material collection volume 206 prior to encountering the mouth 123 of the filter element 170. FIG. 13 shows that the mouth 123 is defined at the axis, $A_M$, and the bore of the fitting 112 is defined at the axis, $A_B$. A length of the material collection volume 206, $L_{SV}$, may be defined between the axes $A_B$, $A_M$. The length may be within the range of 25 to 250 mm, within the range of 50 to 125 mm, within the range of 25 to 75 mm, or within the range of 15 to 50 mm.

An exemplary operation includes the waste collection unit 20 being prepared for use by inserting the manifold 168 within the manifold receiver 40. The tabs 95, 97 are aligned with slots 43, 45 (referring back to FIG. 3) and inserted toward proximal end of the slots 43, 45. The blisters 203 abut the inner surface of collar 41 such that, when the manifold 168 is inserted and then rotated in the grooves 47, the compression of the blisters 203 against the collar 41 imposes a resistive force in opposition to the axial and rotational movement of the manifold 168. When the tabs 95, 97 are fully seated in the slots 43, 45, the manifold 168 is rotated until the tabs 95, 97 reach the end of the grooves 47 internal to the collar 41 of the manifold receiver 40. The components are arranged relative to each other such that, as the tabs 95, 97 rotate to the end of the grooves 47, the blisters 205 rotate into the slots 43, 45 and thus, the blisters 203 no longer abut the collar 41. The consequent removal of the resistive force from the blisters 203 provides a tactile indication that the manifold 168 is secured in the manifold receiver 40. Owing to the orientation of the manifold 168 when coupled with the manifold receiver 40, the material collection volume 206 is located below the filter element 170 relative to the longitudinal axis and the gravity plane. At least one suction line 50 is coupled to at least one of the fittings 112. The suction applicator 48 may be coupled to the suction line 50.

The pump 58 is actuated to draw waste away from the surgical site. The actuation of the pump 58 results draws a waste stream through the suction applicator 48 and suction line 50 into the manifold 168, represented by arrow 222 in FIG. 17. Based on the position of the material collection volume 206, the fluid stream with the material 150 does not immediately encounter the filter element 170. At least some of the material 150 may descend towards and collect within the material collection volume 206 prior to encountering the mouth 123 of the filter element 170. The semisolid and solid matter entrained with the fluid path is captured with the porous features 194 of the filter element 170, and the fluid is drawn into one of the canisters 28, 30 in fluid communication with the manifold volume 65. Further, subsequent to at least some of the porous features 194 of the filter element 170 clogging with the material 150 entrained within the fluid, the material 150 collects within the material collection volume 206 near the bottom of the manifold 168 as opposed to, for example, further accumulating within the filter element 170. With the porous features 194 advantageously disposed an annularly about the head 184, neck 182, basket 174 and/or base 172 of filter element 170, suction through the filter element 170 is maintained even as lower portions of the porous features 194 become occluded. The manifold 168 should continue to operate until substantially an entirely of the volume within the housing 62 is consumed with semisolid and solid material. Only then is it more likely that the material 150 will clog the porous feature 194 of the uppermost portion of the filer element 170. As a result, substantially an entirety of the volume within the manifold 168 is utilized, extending the operating life of the manifold 168.

III. Third Embodiment

Figure 18:
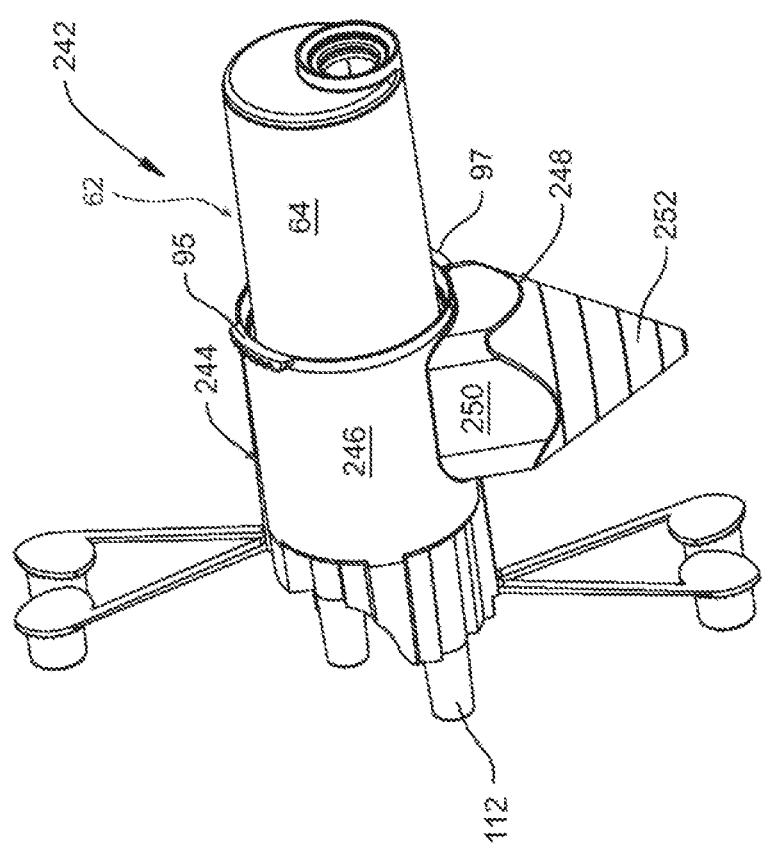
FIG. 18 is a perspective view of the manifold in accordance with another exemplary embodiment of the present disclosure.
Figure 19:
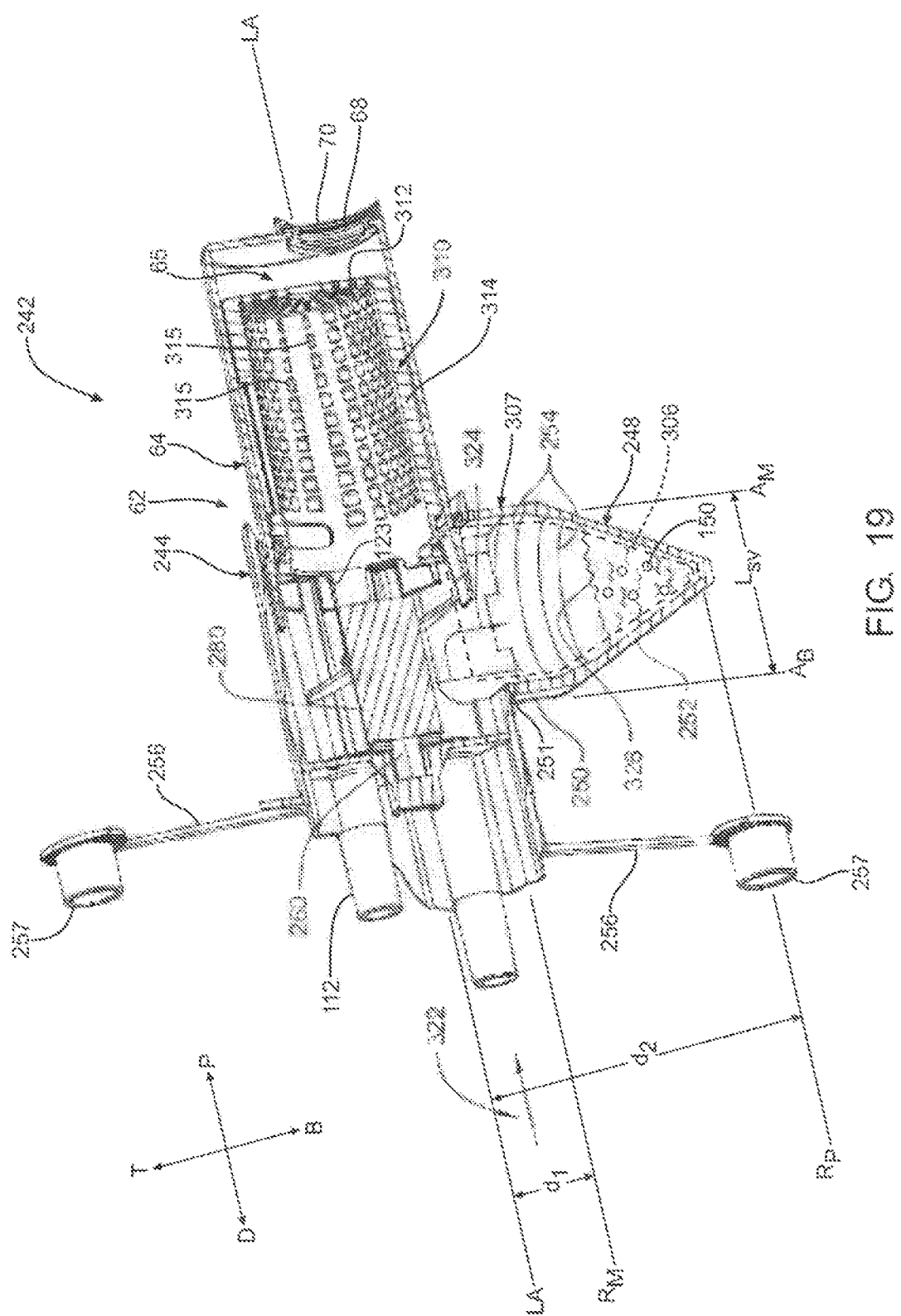
FIG. 19 is a sectional view of the manifold of FIG. 18.
Figure 21:
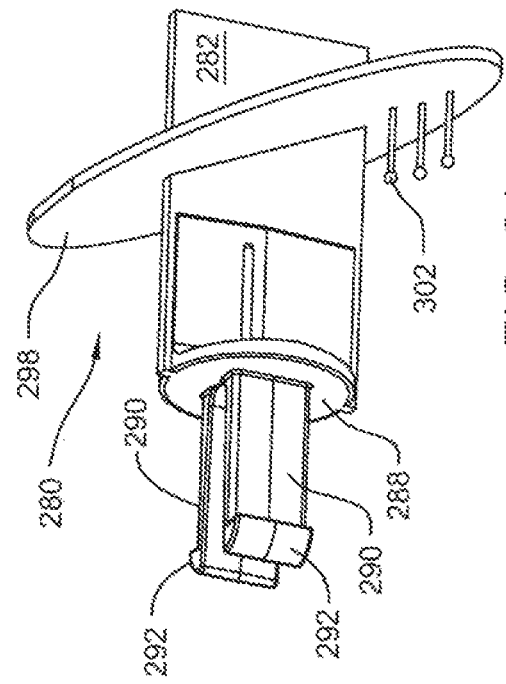
FIG. 21 is a perspective view of a flow diverter.
Figure 20:
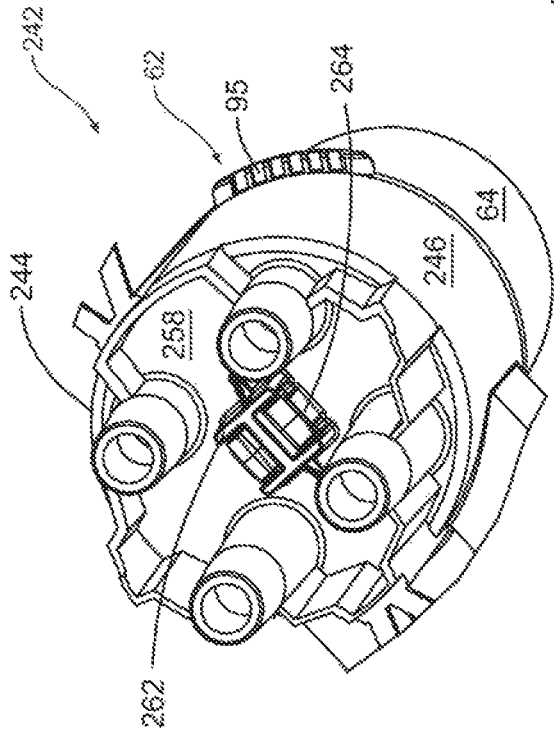
FIG. 20 is a distal perspective view the manifold of FIG. 18.

FIGS. 18-20 show a manifold 242 in accordance with another exemplary embodiment of the present disclosure. Similarly numbered structures from the previously described embodiments of the manifold 60, 168 are herein incorporated by reference for the present embodiment of the manifold 242 to be described. The manifold 242 includes the proximal portion 64 and a distal portion 244. The proximal and distal portions 64, 244 collectively define the housing 62 of the manifold 242. The distal portion 244 is similar in at least some respects to the distal portions 88, 202 previously described, for example, the distal portion 244 includes a neck 246 that is generally cylindrical in shape. The manifold 242 includes a face plate 258 defining a distal end of the manifold 242. The fittings 112 and fence section 114 extend forward from face plate 258. The fittings 112 define the bore in communication with the manifold volume 65 within the manifold 242. Plural tethers 256 are shown extending from the face plate 258 with two pairs of tethers identified in FIG. 18. A fitting distal portion 257 is attached to a free end of each of the tethers 256 with the distal portions 257 configured to cover the bore of the fitting 112 through which suction is not being drawn to eliminate suction loss through that fitting. While not illustrated, it is understood that previously described manifolds 60 and 168 are typically provided with similar tethers and fitting distal portions.

The manifold 242 includes a filter element 310 having a basket 314. The basket 314 may be substantially cylindrical. The basket 314 extends between a base 312 defining a proximal end of the filter element 310, and the mouth 123 opposite the base 312 defining a distal end of the filter element 310. The basket 314 is sized and shaped to be positioned within the housing 62, and more particularly the proximal portion 64 of the housing 62. The filter element 310 includes features (not identified in FIG. 19) that engage the proximal portion 64 so as to hold the filter element 310 to the proximal portion 64, including but not limited to those introduced with the previously described embodiments. The filter element 310 further includes porous features 315. The porous features 315 may be disposed within the base 312 and/or the basket 314. The porous features 315 are generally sized so as to trap material entrained within the fluid as the fluid is drawn across the filter element 310. With the filter element 310 disposed within the housing 62 and the suction line 50 coupled to the fitting 112, a fluid communication path is established from the bore of the fitting 112 to the outlet opening 68 through the manifold volume 65 and across the filter element 310. The porous features 315 trap the material entrained within the fluid as the fluid is drawn through the fluid communication path. With extended or repeated use over time, the porous features 315 of the filter element 310 may partially or completely clog with the semi-solid and solid matter entrained within the fluid, possibly resulting in drop in suction across the manifold 242 and/or at the surgical site.

The present embodiment of the manifold 242 includes a material collection volume 306 in many respects similar to the material collection volumes 106, 206 of the exemplary embodiments previously described (see FIGS. 5 and 13). With reference to FIG. 19, the distal portion 244 of the manifold 242 includes the longitudinal axis LA extending proximally from the distal end of the distal portion 202 and oriented proximally (P) to distally (D) to define a top direction (T) and a bottom direction (B). The material collection volume 306 is located below a bottom of the basket 314 of the filter element 310 relative to horizontal. In other words, the material collection volume 306 is located opposite the basket 314 of the filter element 310 relative to the longitudinal axis LA. With the material collection volume 306 below the bottom of the basket 314, the material 150 descending into and collecting with the material collection volume 306 is effectively removed from the fluid communication path.

The material collection volume 306 is defined by a protrusion 307. With continued reference to FIG. 19, the bottom of the basket 314 is defined on the axis, $R_M$, at the first distance, $d_1$, from the longitudinal axis LA, and the protrusion 307, and more particularly a bottom of the protrusion 307 is at the second distance, $d_2$, from the longitudinal axis LA. The second distance is greater than the first distance with the difference defining a depth of the material collection volume 306. In another convention, the depth of the material collection volume 306 is defined between a first distance from the longitudinal axis LA to the sidewall of the housing 62, and the second distance, $d_2$, from the longitudinal axis LA to the bottommost portion of the protrusion 307 (i.e., a depth of the protrusion 307). The depth of the material collection volume 306 may be configured to provide sufficient capacity for the material 150, for example, at least 5 mm, at least 10 mm, at least 20 mm, at least 50 mm, or at least 100 or more millimeters. Alternatively, the depth of the material collection volume 306 may range from 5 to 100 mm, 10 to 75 mm, or 20 to 50 mm. It is understood, however, that the depth of the material collection volume 306, may be designed based on the dimensional constraints of the housing 62 and/or the needs of the surgical application. The volume of the material collection volume 306 may be at least 5, 6, 7, 8, 9, or 10 cm$^3$. Alternatively, the volume of the material collection volume 306 may range from 1 to 10, 3 to 8, or 4 to 6 cm$^3$. In certain embodiments, the ratio of the volume of the material collection volume 306 to the manifold volume 65 ranges from 1:3 to 1:8, from 1:3 to 1:6, or from 1:4 to 1:5. Alternatively, the manifold volume 65 may be at least 2, 3, 4, 5, or 6 times the volume of the material collection volume 306.

The material collection volume 306 is at least partially located distal to the filter element 310. More specifically, the material collection volume 306 is at least partially located distally to the mouth 123 of the filter element 170, and even more specifically, axially between a proximal end of the bore of the fitting 112 and the mouth 123 of the filter element 170. With the material collection volume 306 distal to the mouth 123, the material 150 descends and collects within the material collection volume 306 prior to encountering the mouth 123 of the filter element 310. FIG. 5 shows that the mouth 123 is defined at the axis, $A_M$, and the bore of the fitting 112 is defined at the axis, $A_B$. The length of the material collection volume 307, $L_{SV}$, may be defined between the axes $A_B$, $A_M$. The length may be within the range of 1.0 to 10.0 inches, or more particularly within the range of 2.0 to 5.0 inches.

In the embodiment illustrated in FIGS. 18 and 19, the manifold 242 includes a tissue trap 248 including the protrusion 307 and at least partially defining the material collection volume 306. The tissue trap 248 projects laterally outwardly from the sidewall of the housing 62, and more particularly the proximal portion 64 of the housing 62. In certain embodiments, the tissue trap 248 comprises a portion of the housing 62, and in other embodiments, the tissue trap 248 is removably coupled to the housing 62. For example, each of the tissue trap 248 and the housing 62 may include complementary coupling features 251 adapted to removably couple the tissue trap 248 from the proximal portion 64 of the housing 62. The complementary coupling features 251 may include threading, detents, friction fit, and the like. In such an example, decoupling the tissue trap 248 from the housing 62 may provide for retrieval of the material collected within the tissue trap 248. It is contemplated that the tissue trap 248 of the manifold 242 of the present embodiment may be included on the embodiments of the manifold 60, 168 previously described. The tissue trap 248 may include an upper portion 250 and a lower portion 252. The upper portion 250 may be in the form of a rectangular-shaped tube. The lower portion 252 of the tissue trap 248 may be substantially conical, as shown in FIGS. 18 or 19, substantially pyramidal, or other suitable shapes to provide for the material collection volume 306 of desired volume and profile. The tissue trap 248 may be formed from materials that are partially or entirely transparent and further include graduations 254 indicating a volume of the trap from the bottom of the lower portion 252. The graduations 254 facilitate identifying the volume of material and fluid collected within the tissue trap 248. While the tissue trap 248 imparts a profile to the manifold 242 distinct from the previously described embodiments and defines a relatively larger material collection volume 306, in many respects the function is similar across the three embodiments. The material collection volume 306 is positioned within the housing 62 such that the material 150 deposits and collects within the material collection volume 306. With the material 150 collected and settled within the material collection volume 306, less material enters the filter element 310 to potentially occlude the porous features 315. The manifold 242 is thus configured to accommodate more fluid and more material within the fluid path prior to requiring replacement. It is understood that the tissue trap 248 may be provided within the other exemplary embodiments of the manifold 60, 168 of the present disclosure, or embodiments of a manifold not including a material collection volume.

With the tissue trap 248 providing for the material collection volume 306 with a larger capacity, it may be desirable to direct the fluid flow towards the tissue trap 248 prior to encountering the mouth 123 of the filter element 310. The manifold 242 may further include a flow diverter 280 positioned with the housing 62. The flow diverter 280 is axially located between the bore of the fitting 112 and the mouth 123 of the filter element 310 to be positioned within the fluid communication path. The flow diverter 280 is configured to direct at least a portion of the fluid and the material 150 being drawn through the fluid communication path towards the material collection volume 306. With reference to FIGS. 10-23, the face plate 258 is further formed to have two openings 260, one of which is identified in FIG. 19. An H-shaped beam 262 protrudes outwardly from the face plate 258 with the center web of the beam 262 located between the openings 260 and the opposed parallel wings of the beam 262 located adjacent the sides of the openings 260. One or more tabs 264 may also project outwardly from the face plate 258 with each of the tabs 264 located adjacent one of the openings 260. The tabs 264 are located between the free ends of the wings of beam 262 that surround the opening 260.

The flow diverter 280 includes a center panel 282. In the illustrated example, the center panel 282 is planar and rectangular-shaped. The center panel 282 is generally oriented parallel to the longitudinal axis LA. A circular head 288 is secured to the distal end of the center panel 282. The head 288 is disposed in a plane that is perpendicular to the plane of the center panel 282. The flow diverter 280 includes ears 290 extending distally forward from the top of head 288. The ears 290 may be generally in the form of parallel posts each with a rectangularly-shaped cross sectional profile. Each ear 290 is further shaped to have a tip 292 that projects a short distance outwardly. When the manifold 242 is assembled, each of the ears 290 is inserted through a separate one of the openings 260 in the face plate 258 of the distal portion 244. Each of the tips 292 of the ears 290 projects over a separate one of the tabs 264 of the distal portion 244. The ear-over-tab engagement secures the flow diverter 280 with the manifold volume 65 internal to the distal portion 244 of the housing 62. Owing to the dimensioning of the components forming the manifold 242, when the flow diverter 280 is so secured in place, the distally directed surface of head 288 presses against the adjacent proximally directed surface of the face plate 258. It is appreciated that the flow diverter 280 may be of unitary construction and formed from relatively inexpensive materials such as plastic.

The flow diverter 280 further comprises a baffle 298. The baffle 298 extends outwardly front the center panel 288. The baffle 298 may be circular with a diameter greater than the bottom-to-top height of the center panel 282. An orientation of the baffle 298 is disposed at an oblique angle relative to the longitudinal axis LA. As shown in FIG. 19, a top of the baffle 298 (i.e., in the top direction (T)) is positioned distally relative to a bottom of the baffle 298 (i.e., in the bottom direction (B)). Stated differently, the baffle 298 is angled relative to the longitudinal axis LA such that, as the baffle 298 extends downwardly towards the tissue trap 248, the bottom of the baffle 298 angles proximally towards the proximal portion 64. Owing to the size, shape, and orientation of the baffle 298, the flow diverter 280 is configured to direct at least a portion, and often most of the fluid and the material being drawn through the fluid communication path towards the material collection volume 306. In other words, a substantial fraction of the waste stream contacts the distally directed face of baffle 298, which diverts the waste stream into the tissue trap 248. It may be considered in some instances that the fluid communication path includes the material collection volume 306, as represented by arrow 324 in FIG. 19, however, it is understood that the flow diverter 280 may be provided within the exemplary embodiments of the manifold 60, 168 previously described, or embodiments of a manifold not including a material collection volume.

With much of the waste stream contacting the distal face of the baffle 298, the flow diverter 280 may include retention members 302 coupled to the distal face. The retention members are adapted to retain debris within the fluid communication path, for example, sutures, pieces of tissue, and other lengthier pieces of debris. In the illustrated embodiment of FIG. 21, the retention members 302 are pins.

An exemplary operation includes the waste collection unit 20 being prepared for use by inserting the manifold 242 within the manifold receiver 40. The tabs 95, 97 are positioned to engage the grooves 47 (see FIG. 3) internal to the collar 41 of the manifold receiver 40, and rotation of the manifold 242 releasably locks the manifold 242 to the manifold receiver 40. As a result of the positioning of the components forming the system, when the manifold 242 is in this locked state, the manifold 242 is in a rotational orientation about the longitudinal axis LA such that the trap 248 is below the longitudinal axis LA. More particularly, the manifold 242 is oriented so the bottom of the tissue trap 248 is lowest relative to the gravity plane, and the material collection volume 306 is located below the filter element 310. At least one suction line 50 is coupled to at least one of the fittings 112. The suction applicator 48 may be coupled to the suction line 50.

The pump 58 is actuated to draw waste away from the surgical site. The actuation of the pump results draws a waste stream through the suction applicator 48 and suction line 50 into the manifold 242, represented by arrow 322 in FIG. 19. Based on the position of the material collection volume 306, at least some of the material 150 descends towards and collect within the material collection volume 306 prior to encountering the mouth 123 of the filter element 310. The fluid is drawn into one of the canisters 28, 30 in fluid communication with the manifold volume 65. Further, the fluid and the material being drawn through the fluid communication path towards the material collection volume 306 contacts the distal face of baffle 298, which diverts the waste stream into the tissue trap 248. Subsequent to at least some of the porous features 315 of the filter element 310 clogging with the material 150 entrained within the fluid, the material 150 may collect within the material collection volume 306 near the bottom of the manifold 242.

It is further contemplated that the waste collection system 20 may be operated in one of a low suction mode and a high suction mode. In the low suction mode with relatively low suction being drawn through the suction line 50, substantially an entirety of the waste stream (i.e., the fluid and the material) enters the tissue trap 248, represented by wave line 326 in FIG. 19. However, the level of suction is insufficient to draw the material out of the tissue trap 248. The graduations 254 on the at least partially transparent tissue trap 248 may be used to measure the volume of waste withdrawn from the surgical site. This feature may be particularly useful in some procedures, such as pediatric procedures and ophthalmic procedures, in which the only a small volume of material is withdrawn, for example, ten cubic centimeters or less of material. In the low suction mode, the tissue trap 248 may ultimately become filled with the waste stream. While the graduations 254 may no longer be useful for measuring the volume of the waste stream, the density of the material 150 relative to the fluid results in the material descending towards and collecting within the bottom of the material collection volume 306 defined by the tissue trap 248. Subsequently, should higher levels of suction be applied through the manifold 242, the fluid is drawn from within the tissue trap 248 while the material remains settled within the material collection volume 306. With less of the material encountering the filter element 310, the likelihood of clogging of the filter element 310 is reduced and the operating life of the manifold 242 is extended.

In a high suction mode with relatively high suction being drawn through the suction line 50, substantially an entirety of the waste stream (i.e., the fluid and the material) may contact and be diverted by the distal face of the baffle 298. The level of suction is sufficient to draw the fluid around the baffle 298 and into the mouth 123 of the filter element 310 while the material 150 descends towards and collects within the bottom of the material collection volume 306 defined by the tissue trap 248. Any semisolid and solid matter entrained with the fluid path entering the mouth 123 of the filer element 310 is captured with the porous features 315 of the filter element 310, and the fluid is drawn into one of the canisters 28, 30 in fluid communication with the manifold volume 65. Subsequent to at least some of the porous features 315 of the filter element 310 clogging with the material 150 entrained within the fluid, the material 150 may collect within the material collection volume 306 near the bottom of the manifold 242.

IV. Alternative Embodiments

The foregoing is directed to specific embodiments of the disclosure to which this application is directed. Alternative embodiments are possible. For example, the described mobile unit used as part of a system of this disclosure is exemplary, not limiting. Not all waste collection units integrated into this system may be mobile or include two waste collection unit canisters. Similarly, other versions of the system of this disclosure may include alternative features for ensuring that, when the manifold is fitted to the waste collection unit the manifold is in the proper orientation relative to the gravity plane. For example, it is within the scope of this disclosure that the waste collection unit may include one or more alignment tabs with the manifold housing formed with a complementary number of slots. The slots may be positioned so that the manifold must be orientated so the tabs seat in the slots to provide the correct orientation. Still in other aspects of the disclosure, it may be desirable to provide the manifold receiver with an asymmetric bore and the manifold housing with complementary asymmetric shapes. This would again ensure that, as a result of the sealing of the manifold in the bore, the manifold has the correct orientation.

Not all features may be present in all versions of the disclosure. By way of example, some manifolds of this disclosure may only have a single fitting for receiving a suction line. Likewise, it may not always be necessary to fit a drip stop in the outlet opening of the manifold housing. In versions of the disclosure in which a tissue trap is present to provide a means for determining the volume of withdrawn waste, it may not be necessary to provide the manifold with a filter. Not all versions of manifold may include the blisters. The blister may be incorporated in manifolds other than the second described embodiment. In regard to this aspect of the disclosure, it may be possible to provide a manifold with a single blister or three or more blisters to provide the desired tactile feedback. A filter with a snorkel section may be incorporated into manifolds of the second and third embodiments as well as manifolds that do not include a settling chamber. The various features of the manifold of the present disclosure may likewise be combined. It is within the scope of this disclosure that the tissue trap and flow diverter may separately or together be included on the first and second embodiments of the manifold. Likewise, the tissue trap and flow diverter may separately or together be combined with any of the disclosed filter elements.

The structure of the flow diverter used to direct the waste stream into the tissue trap may be different from what has been described. In some aspects of the disclosure, the flow diverter may be a set of one or more panels molded into the manifold housing. The panels include surfaces that are positioned to direct the waste stream into the tissue trap prior to the waste stream flowing through the filter element and the outlet opening. Similarly, as an alternative to pins, the retention feature on the flow diverter may be a non-linear surface with indentations. The indentations may serve as a pocket in which waste that would otherwise be trapped by the filter is trapped.

Several embodiments have been discussed in the foregoing description. However, the embodiments discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

What is claimed is:

1. A manifold for a medical/surgical waste collection system, said manifold comprising:
    a housing comprising at least one sidewall defining a manifold volume, and a distal portion defining a distal end and comprising a longitudinal axis extending proximally from said distal end of said distal portion;
    an outlet opening within a proximal portion of said housing and in fluid communication with said manifold volume;
    a filter element within said housing and comprising a base, a mouth positioned opposite said base relative to said outlet opening, a basket extending between said base and said mouth, and porous features within said basket;
    at least one fitting defining a bore in fluid communication with said manifold volume with said fitting adapted to receive a suction line for drawing fluid into said manifold volume, wherein a fluid communication path is established from said bore of said fitting to said outlet opening through said manifold volume and across said filter element such that said porous features are adapted to trap material entrained within the fluid as the fluid is drawn through said fluid communication path; and
    a protrusion extending downwardly from said at least one sidewall to at least partially define a material collection volume within said housing with said material collection volume at least partially located axially between said bore of said fitting and said mouth of said filter element, and further located below a bottom of said basket of said filter element relative to said longitudinal axis such that, as the fluid and the material is drawn through said fluid communication path, the material collects within said material collection volume.

2. The manifold of claim 1, wherein said protrusion further comprises a first surface extending downwardly from said at least one sidewall, and a second surface extending distally from said first surface to said distal end of said housing with said first and second surfaces defining at least a portion of said material collection volume.

3. The manifold of claim 1, further comprising a tissue trap comprising said protrusion with said tissue trap and said housing comprising complementary coupling features to removably couple to said tissue trap with said housing to permit retrieval of the material collected within said material collection volume.

4. The manifold of claim 1, further comprising a flow diverter within said housing and located axially between said bore of said fitting and said mouth of said filter element to be positioned within said fluid communication path with said flow diverter adapted to direct at least a portion of the fluid and the material being drawn through said fluid communication path towards said material collection volume.

5. The manifold of claim 1, wherein said filter element further comprises a snorkel comprising porous features coupled to said basket and at least partially located axially between said bore of said fitting and said mouth of said filter element, and further located opposite the material collection volume relative to said longitudinal axis with each of said basket;
wherein said snorkel comprises a tubular wall and a distal face coupled at an end of said tubular wall.

6. The manifold of claim 5, wherein said basket defines a basket void space and said snorkel defines a snorkel void space with said void spaces in fluid communication with said outlet opening and separate from one another, wherein a second fluid communication path is established from said bore to said outlet opening through said snorkel void space.

7. The manifold of claim 1, wherein said protrusion comprising a transition, and a surface coupled to said transition and located at a second distance from said longitudinal axis with said second distance being greater than a first distance such that, as the fluid and material is drawn through said fluid communication path, the material collects within said material collection volume prior to encountering said mouth of said filter element.

8. A manifold for a medical/surgical waste collection system, said manifold comprising:
a housing comprising at least one sidewall defining a manifold volume;
an outlet opening in fluid communication with said manifold volume;
a filter element within said housing and comprising a base, a mouth positioned opposite said base relative to said outlet opening, a basket extending between said base and said mouth, and porous features within said basket;
at least one fitting defining a bore in fluid communication with said manifold volume with said fitting adapted to receive a suction line for drawing fluid into said manifold volume, wherein a fluid communication path is established from said bore of said fitting to said outlet opening through said manifold volume and across said filter element such that said porous features of said filter element are adapted to trap material entrained within the fluid as the fluid is drawn through said fluid communication path; and
a tissue trap removably coupled to a distal portion of said housing and at least partially located axially between said bore of said at least one fitting and said mouth of said filter element with said tissue trap defining a material collection volume below said filter element such that, as the fluid and the material is drawn through said fluid communication path, the material collects within said tissue trap; and
a flow diverter within said housing and axially located between said bore of said fitting and said mouth of said filter element to be positioned within said fluid communication path with said flow diverter adapted to direct at least a portion of the fluid and the material being drawn through said fluid communication path towards said material collection volume.

9. The manifold of claim 8, wherein said tissue trap and said housing further comprise complementary coupling features to removably couple to said tissue trap with an exterior of said housing to permit retrieval of the material collected within said tissue trap.

10. The manifold of claim 8, wherein said tissue trap is at least partially transparent and further comprises graduations for identifying a volume of the material collected within said tissue trap.

11. The manifold of claim 8, wherein said filter element further comprises a snorkel coupled to said basket and at least partially located axially between said bore of said fitting and said mouth of said filter element, and further located opposite the material collection volume relative to a longitudinal axis with each of said basket and said snorkel comprising said porous features.

12. The manifold of claim 11, wherein said basket defines a basket void space and said snorkel defines a snorkel void space with said void spaces in fluid communication with said outlet opening and separate from one another, wherein a second fluid communication path is established from said bore to said outlet opening through said snorkel void space.

13. A manifold for a medical/surgical waste collection system, said manifold comprising:
a housing comprising at least one sidewall and a faceplate collectively defining a manifold volume, wherein a longitudinal axis of said manifold extends proximally from said faceplate;
an outlet opening within a proximal portion of said housing and in fluid communication with said manifold volume;
a filter element within said housing and comprising a base, a mouth positioned opposite said base relative to said outlet opening and spaced apart from said faceplate, a basket extending between said base and said mouth, and porous features within said basket, wherein a bottom of said basket is defined on an axis at a first distance from said longitudinal axis;
at least one fitting defining a bore in fluid communication with said manifold volume with said fitting adapted to receive a suction line for drawing fluid into said manifold volume, wherein a fluid communication path is established from said bore of said fitting to said outlet opening through said manifold volume and across said filter element such that said porous features are adapted to trap material entrained within the fluid as the fluid is drawn through said fluid communication path; and
a protrusion extending from said at least one sidewall to at least partially define a material collection volume within said housing, said protrusion comprising a transition, and a surface coupled to said transition and located below said mouth of said filter element at a second distance from said longitudinal axis with said second distance being greater than said first distance such that, as the fluid and material is drawn through said fluid communication path, the material collects within said material collection volume prior to encountering said mouth of said filter element;
wherein said filter element further comprises a snorkel coupled to said basket and said basket defines a basket void space and said snorkel defines a snorkel void space with said void spaces in fluid communication with said outlet opening and separate from one another, wherein a second fluid communication path is established from said bore to said outlet opening through said snorkel void space; and further comprising a flow diverter within said housing and axially located between said bore of said fitting and said mouth of said filter element to be positioned within said fluid communication path with said flow diverter adapted to direct at least a portion of the fluid and the material being drawn through said fluid communication path towards said material collection volume.

14. The manifold of claim 13, wherein a depth of said material collection volume is defined between a difference of said first distance and said second distance.

15. The manifold of claim 14, wherein a length of said material collection volume is defined between said faceplate and said mouth of said filter element.

16. The manifold of claim 13, wherein said surface of said protrusion is a first surface and said transition comprising a second surface extending distally from said first surface, wherein said first surface and said second surface at least partially define said material collection volume.

17. The manifold of claim 13, wherein said protrusion is removably coupled with a tissue trap, wherein said at least one sidewall of said housing comprises complementary coupling features to removably couple said tissue trap with said protrusion in said at least one sidewall of said housing to permit retrieval of material collected within the material collection volume without complete disassembly of the housing.

18. The manifold of claim 13, wherein said snorkel is at least partially located axially between said bore of said fitting and said mouth of said filter element, and further located opposite the material collection volume relative to said longitudinal axis with each of said basket and said snorkel comprising porous features.

\* \* \* \* \*